US012611478B2

(12) United States Patent
Landgrebe et al.

(10) Patent No.: US 12,611,478 B2
(45) Date of Patent: Apr. 28, 2026

(54) DETERMINING EFFECTIVENESS OF STERILIZATION PROCEDURE FROM OUTSIDE THE STERILIZATION PACKAGE

(71) Applicant: Solventum Intellectual Properties Company, Maplewood, MN (US)

(72) Inventors: Kevin D. Landgrebe, Woodbury, MN (US); G. Marco Bommarito, Stillwater, MN (US); Timothy J. Nies, Stillwater, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 770 days.

(21) Appl. No.: 17/907,555

(22) PCT Filed: Mar. 17, 2021

(86) PCT No.: PCT/IB2021/052235
§ 371 (c)(1),
(2) Date: Sep. 28, 2022

(87) PCT Pub. No.: WO2021/198831
PCT Pub. Date: Oct. 7, 2021

(65) Prior Publication Data
US 2023/0142866 A1      May 11, 2023

Related U.S. Application Data

(60) Provisional application No. 63/004,871, filed on Apr. 3, 2020.

(51) Int. Cl.
*A61L 2/28* (2006.01)
*A61L 2/07* (2006.01)
(Continued)

(52) U.S. Cl.
CPC .................................... *A61L 2/28* (2013.01); *A61L 2/07* (2013.01); *A61L 2/206* (2013.01); *A61L 2/208* (2013.01);
(Continued)

(58) Field of Classification Search
CPC ...... A61B 2050/005; A61B 2050/0057; A61B 2050/0067; A61B 50/30; A61L 2/07;
(Continued)

(56) References Cited

U.S. PATENT DOCUMENTS

| | | | |
|---|---|---|---|
| 4,612,872 A | 9/1986 | Whelchel et al. | |
| 7,300,637 B2 | 11/2007 | Lin et al. | |

(Continued)

FOREIGN PATENT DOCUMENTS

| | | |
|---|---|---|
| WO | 2010054095 A1 | 5/2010 |
| WO | 2014150048 A1 | 9/2014 |

(Continued)

OTHER PUBLICATIONS

International Search Report for PCT International Application No. PCT/IB2021/052235, mailed on Oct. 15, 2021, 4 pages.

*Primary Examiner* — Jennifer Wecker
*Assistant Examiner* — Jonathan Bortoli

(57) ABSTRACT

An example sterilization indicator (102) includes a cover (122), an indicator (102), and a seal (142). The cover (122) defines at least a portion of a cavity (138). The indicator (102) is disposed within the cavity (138). The indicator (102) is configured to fluidly couple with an internal cavity (110) of a sterilization package (package) and indicate an exposure to a sterilant. The seal (142) is configured to form a microorganism barrier between an exterior of the cover (122) and an internal cavity (110) of a sterilization package (100).

20 Claims, 15 Drawing Sheets

(51) Int. Cl.

| | |
|---|---|
| *A61L 2/20* | (2006.01) |
| *A61L 2/206* | (2026.01) |
| *A61L 2/208* | (2026.01) |
| *B65D 79/02* | (2006.01) |

(52) U.S. Cl.
CPC .......... *B65D 79/02* (2013.01); *A61L 2202/18* (2013.01); *A61L 2202/24* (2013.01)

(58) Field of Classification Search
CPC . A61L 2/206; A61L 2/208; A61L 2/28; A61L 2202/18; A61L 2202/24; B65D 79/02; G01N 31/226; A63B 2071/026; A63B 2225/09; A63B 2225/093; A63B 69/22; A63B 69/305; A63C 1/00
See application file for complete search history.

(56) References Cited

U.S. PATENT DOCUMENTS

| | | | |
|---|---|---|---|
| 8,470,601 B2 | 6/2013 | Foley et al. | |
| 2002/0039792 A1* | 4/2002 | Hehenberger | ............ A61L 2/28 436/1 |
| 2016/0022853 A1* | 1/2016 | Hajime | ................ G01N 31/222 206/370 |

FOREIGN PATENT DOCUMENTS

| | | | |
|---|---|---|---|
| WO | 2017044906 A2 | 3/2017 | |
| WO | 2020222054 A1 | 11/2020 | |

* cited by examiner

DETERMINING EFFECTIVENESS OF STERILIZATION PROCEDURE FROM OUTSIDE THE STERILIZATION PACKAGE

CROSS REFERENCE TO RELATED APPLICATIONS

This application is a national stage filing under 35 U.S.C. 371 of PCT/IB2021/052235, filed Mar. 17, 2021, which claims the benefit of U.S. Application No. 63/004,871, filed Apr. 3, 2020, the disclosure of which is incorporated by reference in its/their entirety herein.

TECHNICAL FIELD

The present application is related to articles, systems, and techniques for determining the effectiveness of a sterilization procedure from outside the sterilization package.

BACKGROUND

Medical instruments are cleaned, assembled, processed, packaged, stored, and issued for patient care from the central sterilization department or Sterile Processing Department of a hospital. Typically, once opened in the operating room or other point of use, sterilization indicators placed inside sterilization packages prior to sterilization are used to determine whether instruments inside the sterilization package were properly sterilized.

SUMMARY

The disclosure is related to articles, systems, and techniques for determining, by an indicator disposed on an exterior of a sterilization package, the effectiveness of a sterilization procedure. The described articles, systems, and techniques include externally visible, internally sampling sterilization indicators configured to enable assessment of the presence and state of a chemical indicator prior to taking medical instruments to the operating room.

In some examples, the disclosure is directed to a sterilization indicator including a cover, an indicator, and a seal. The cover defines at least a portion of a cavity. The indicator is disposed within the cavity. The indicator is configured to fluidly couple with an internal cavity of a sterilization package and indicate an exposure to a sterilant. The seal is configured to form a microorganism barrier between an exterior of the cover and an internal cavity of a sterilization package.

In some examples, the disclosure is directed to a sterilization package including an enclosure, and a sterilization indicator disposed on the exterior surface of the enclosure. The enclosure includes an exterior surface and defines an internal cavity. At least a portion of the enclosure comprises a sterilant-permeable region. The sterilization indicator includes cover, an indicator, and a seal. The cover defines at least a portion of a cavity. The indicator is disposed within the cavity and is fluidly coupled to the internal cavity of the enclosure. The indicator is configured to indicate an exposure to a sterilant within the internal cavity. The seal is configured to form a microorganism barrier between an exterior of the enclosure and the internal cavity of the enclosure.

In some examples, the disclosure is directed to a method of forming a sterilization indicator. The method includes forming a cover defining at least a portion of a cavity. The method also includes positioning an indicator within the cavity. The indicator is configured to fluidly couple with an internal cavity of a sterilization package and indicate an exposure to a sterilant. The method also includes disposing a seal adjacent the cover. The seal is configured to form a microorganism barrier between an exterior of the cover and the cavity of the sterilization package.

In some examples, the disclosure is directed to a method of using a sterilization indicator. The method includes positioning the sterilization indicator on an exterior surface of an enclosure, which defines an internal cavity. At least a portion of the exterior surface comprises a sterilant-permeable region. The method also includes exposing the sterilization indicator and the enclosure to a sterilant for a selected duration of time, at a selected temperature, and/or at a selected sterilant concentration. The method also includes determining, by the indicator, whether the internal cavity of the enclosure was exposed to at least one of a threshold exposure duration, a threshold sterilant temperature, or a threshold sterilant concentration.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

Like symbols in the drawings indicate like elements.

DETAILED DESCRIPTION

Figure 1:
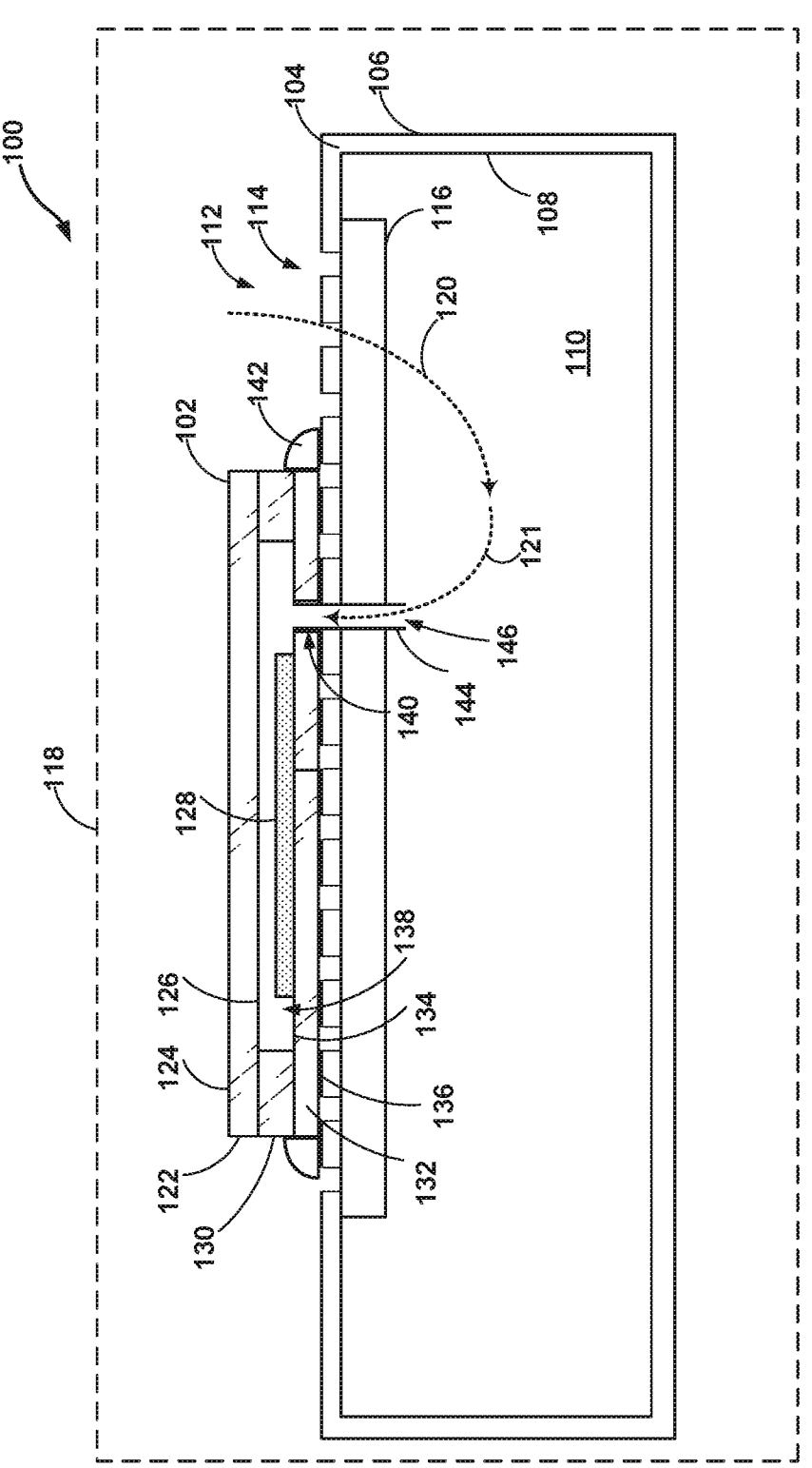
FIG. 1 is a conceptual cross-sectional view of an example sterilization package that includes a sterilization indicator positioned on an exterior surface of an enclosure.

The present disclosure describes articles, systems, and techniques for assessing the presence and condition of sterilization inside a closed sterilization package from outside the closed sterilization package. Such sterilization indicators include externally visible, internally sampling sterilization indicators (hereinafter, sterilization indicators). An example sterilization indicator system may include, for example, a chemical or biological sterilization indicator, a housing surrounding the sterilization indicator, a conduit fluidly coupled to an interior of the housing via a sample port, one or more seals configured to provide a sterile barrier between the interior of the housing and an environment exterior to the housing and sterilization package, and an optional locking mechanism configured to secure the sterilization indicator to the sterilization package in a tamper-resistant manner.

A variety of products and articles, including, for example, medical instruments, devices, bandages, and equipment, must be sterilized prior to use to prevent biocontamination of a wound site, a sample, an organism, or the like. Used medical instruments received from the operating room in the decontamination area of the Sterile Processing Department undergo a sterilization procedure. The used medical instruments are processed by manual and/or automated cleaning and disinfecting procedures, followed by packaging in a soft pack or a rigid container (e.g., a sterilization package). The sterilization package materials and sterilization methods allow for penetration of sterilant through a sterilant-permeable, microorganism-impermeable material during the sterilization process. The sterilization package materials protect the instruments from microorganism contamination during storage and handling.

Typically, internal sterilization indicators (e.g., not externally visible) are placed in the sterilization package prior to sealing the sterilization package. After sealing, the sterilization package is sterilized using a sterilant, such as, for example, steam, ethylene oxide, dry heat, or hydrogen peroxide vapor. After sterilization, instruments are stored, e.g., from a few minutes to several weeks, until needed in the operating room. The internal sterilization indicator provides a visual indication of the effectiveness of a sterilization procedure. Because materials of some sterilization packages are not transparent, visualization of internal sterilization indicators requires opening of the pack or container.

A method for viewing and obtaining information about the functioning of a sterilizer is to use a test pack. A test pack may include a model package constructed to simulate air removal and the penetration of a sterilant in a sterilization package containing instruments. Since the test pack does not usually contain instruments that are to be used in medical procedures, the test pack can be placed in the same sterilization cycles as the instrument sterilization packages, and can be opened and examined following sterilization without compromising any instruments intended for medical procedures. However, a sterilization load often contains a mixture of different types of sterilization packaging, such as wrapped instrument sets, rigid containers, and other sterilization package forms. Each sterilization package may also contain a different amount of materials within the sterilization packaging, thereby limiting the use and construction of a universal test pack. Additionally, varying the number or orientation of sterilization packages in a given sterilization load can also affect sterilization effectiveness for certain types of sterilization packages. The use of multiple test packs designed to simulate a wider range of packaging types and loading conditions may be limited by available space within a sterilizer and/or procedural complexity for a sterilization technician, e.g., in determining which test packs to use for the various combinations of packaging and load levels, which may lead to increased operator error.

One method for viewing and obtaining information from the interior environment of a sterilization package is to place the indicator inside a sterilization package, then open the sterilization package and inspect the sterilization indicator following a sterilization procedure. For example, during set-up of the operating room for a surgical operation, the sterilization package including designated instrument sets are moved into the operating room. Once inside the operating room, the sterilization package may be opened and inspected for the presence of one or more internal sterilization indicators. The internal sterilization indicators may be used to assess whether the sterilization procedure was effective. For example, the internal sterilization indicators may be used to assess whether the internal cavity of the enclosure was exposed to the sterilant for at least one of a threshold exposure duration, a threshold sterilant temperature, or a threshold sterilant concentration. As used herein, the threshold exposure duration, the threshold sterilant temperature, or the threshold sterilant concentration may include commonly accepted threshold values for respective sterilization procedures.

Unless the internal sterilization indicator provides a visual indication that the sterilization procedure was effective, the set of instruments is considered contaminated and must be reprocessed before use. Reprocessing a sterilization package can have undesired consequences, including decreased productivity in the Sterile Processing Department and delayed surgeries. In an emergency situation, hospitals may use immediate-use sterilization, a process which may be less effective than other sterilization procedures. Thus, reducing reprocessing may be advantageous.

Another method for viewing and obtaining information from sterilization indicators regarding the interior environment of a sterilization package is to introduce a transparent or sheer element, such as a window, within the container or wrap through which the indicator can be visualized. Such modification, however, may add significant costs and complexity to manufacture of the sterilization package.

The described sterilization indicator (e.g., externally visible, internally sampling) articles, systems, and techniques allow an operator (e.g., a technician or clinician) to determine, without opening the sterilization package, whether the interior contents of a closed sterilization package have been exposed to a sterilant for a threshold time, a threshold temperature, and/or a threshold concentration. This enables assessing effectiveness of sterilization within the Sterile Processing Department, e.g., before the sterilization package is moved into the operating room. The described articles, systems, and techniques may reduce the cost and/or the delays associated with contaminated sterilization packages being staged in the operating room. Additionally, or alternatively, the described articles, systems, and techniques may reduce the cost and/or improve processing throughput by eliminating use of test packs. Additionally, or alternatively, the described articles, systems, and techniques may reduce sterilization package cost associated with introducing transparent windows in sterilization packages. Additionally, or alternatively, by fluidically connecting a sterilization indicator outside of the tray to contents inside the tray using a sample port, the described articles, systems, and techniques provide externally visible sterilization indicator that may reduce or prevent operator error in not placing internal sterilization indicator(s) inside a sterilization package prior to sterilization.

FIG. 1 is a conceptual cross-sectional view of an example sterilization package 100 that includes a sterilization indicator 102 positioned on an exterior surface 106 of an enclosure 104. Enclosure 104 is configured to receive articles, such as medical instruments, for sterilization. Sterilization indicator 102 is configured to provide an externally visible indication of whether sterilization parameters were met during the sterilization process for the articles.

Enclosure 104 may define one or more of a base, one or more sidewalls, and/or a top or a removable lid. Enclosure 104 includes an exterior surface 106 and interior surface 108. Interior surface 108 defines an internal cavity 110. Internal cavity 110 is size and shaped to receive one or more articles for sterilization. In some examples, internal cavity 110 may be shaped to receive one or more sterilization trays. The sterilization trays may be configured to retain the articles and reduce contact of the articles with interior surface 108 and/or sterilant, such as condensate, that may remain within internal cavity 110 after sterilization.

Enclosure 104 may include a rigid container, a soft pack, or a wrapped sterilization tray. Generally, enclosure 104 may include any material suitable for sterilizing and storing sterilized articles. In examples in which enclosure 104 includes a rigid container, enclosure 104 may include a rigid material, such as, for example, aluminum, stainless steel, or other metals or polymers compatible with steam, ethylene oxide, dry heat, and/or vaporized hydrogen peroxide sterilization. In examples in which enclosure 104 includes a soft pack, enclosure 104 may include a flexible material, such as, for example, a woven or nonwoven fabric, a spunbond-meltblown-spunbond material, a synthetic fabric, a natural fabric, polyethylene, polypropylene, or combinations thereof. In some examples, the flexible material may be selected to have a selected permeability to a selected sterilant, such as steam, ethylene oxide, dry heat, vaporized hydrogen peroxide, or other sterilant. In some examples, the flexible material may include a microorganism barrier layer. For example, the flexible material may be substantially impermeable to microorganisms, such as bacteria, fungi, viruses, or the like. Substantially impermeable may include impermeable or nearly impermeable in accordance with generally accepted sterilization procedure guidelines. For the purposes of this disclosure, rigid materials may include materials that are stiffer (e.g., a greater Young's modulus) relative to flexible materials.

At least a portion of enclosure 104 comprises a sterilant-permeable region 112. The sterilant-permeable region 112 may include at least a region including the flexible material described above in reference to the soft pack enclosure 104. In examples in which enclosure 104 includes a soft pack flexible material, the entirety of enclosure 104 or at least a portion of enclosure 104 may define sterilant-permeable region 112. In examples in which enclosure 104 includes a rigid material, as illustrated in FIG. 1, sterilant-permeable region 112 may include a plurality of apertures 114 and a filter 116. For example, a portion of enclosure 104, such as a sidewall, base, or removable lid of enclosure 104, may define a plurality of apertures 114. Plurality of apertures 114 may be bored or otherwise mechanically formed in enclosure 104. Filter 116 includes a sterilant-permeable, microorganism barrier material. For example, filter 116 may include the flexible material described above in reference to the soft pack enclosure 104. In this way, during sterilization, sterilant may move from sterilization chamber 118 into internal cavity 110 through apertures 114 and filter 116, as illustrated by dashed arrow 120. From internal cavity 110, the sterilant may move into sterilization indicator 102, as illustrated by dashed arrow 121.

Sterilization indicator 102 may include an article containing a sterilant exposure indicator 128 (indicator 128) configured to provide an indication of an exposure to a sterilant from internal cavity 110 (e.g., via dashed arrow 121). Sterilization indicator 102 may include a layered or laminate structure, a molded structure, or combinations thereof. For example, as illustrated in FIG. 1, sterilization indicator 102 may include cover layer 122 and base layer 132 adjacent to indicator 128, and intermediate layer 130 extending between cover 122 and base 132. In some examples, intermediate layer 130 may be integrally formed with either of cover 122 or base 132. In some examples, sterilization indicator 102 may include cover 122 and intermediate layer 130, optionally integrally formed with cover 122, without base 132. In some examples, sterilization indicator 102 may include only cover 122 configured to couple with/to exterior surface 106 of enclosure 104, e.g., using an adhesive or the like.

In some examples, cover 122 may have a rectilinear shape defining an upper surface 124 and a lower surface 126 opposing surface 124 and extending in a plane substantially parallel to a plane of surface 124. Cover 122 may include any material suitable for use in steam, ethylene oxide, dry heat, or vaporized hydrogen peroxide sterilization procedures. In some examples, cover 122 may include a metal, aluminum, anodized aluminum, stainless steel, glass, a polymeric material, polyethylene, polypropylene, polycarbonate, a polyether sulfone, a polyamide-imide, a polyamide, polytetrafluoroethylene, or combinations thereof. At least a portion of cover 122 includes a transparent or semi-transparent material configured to allow visualization of sterilant exposure indicator 128. For example, the entirety of cover 122 may include a transparent material, or a portion, e.g., window, of cover 122 may include a transparent material.

In some examples, base 132 may include a rectilinear shape defining an upper surface 134 and a lower surface 136 opposing surface 134 and extending in a plane substantially parallel to a plane of surface 134. Base 132 may include any one or more of the materials described above in reference to cover 122. In some examples, base 132 may include any one or more of the materials described above in reference to cover 122. In some examples, base 132 may include an adhesive layer and/or a release liner. The adhesive layer may include, for example, a pressure sensitive adhesive, a hot-melt adhesive, a structural adhesive, a thermoplastic, a thermoset polymer, an epoxy, or an adhesive suitable for use in steam, ethylene oxide, dry heat, or vaporized hydrogen peroxide sterilization procedures and selected to adhere to an external surface of a rigid container or a soft pack. In some examples, the adhesive layer may define a seal configured to form a microorganism barrier between an exterior of enclosure 104 and internal cavity 110 of enclosure 104. The release liner may be removable, e.g., from the adhesive layer, prior to positioning sterilization indicator 102 on enclosure 104. For example, cover 122 may be peripherally bonded to base 132 defining a release liner such that indicator 128 is disposed between the release liner and cover 122.

In some examples, intermediate layer 130 may extend between cover 122 and base 132, defining a rectilinear annulus in the plane of surface 126 and surface 134. For example, intermediate layer 130 may define a cavity 138 configured to receive at least a portion of indicator 128. In some examples, at least a portion of intermediate layer 130 may extend between at least a portion of cover 122 and at least a portion of indicator 128, between at least a portion of base 132 and at least a portion of indicator 128, or both.

As one example, indicator 128 may be dimensionally smaller than cover 122 and base 132. In this way, one or more perimeter edges of both cover 122 and base 132 may extend beyond a perimeter of indicator 128. Indicator 128 may be disposed on surface 126 of cover 122 and/or surface 134 of 132. In some examples, indicator 128 may be disposed directly on surface 126 and/or surface 134. In some examples, one or more additional intermediate layers may be disposed between indicator 128 and surface 126 and/or surface 134. For example, the one or more additional intermediate layers may include an adhesive, a filter material, or a fluid.

By extending beyond a perimeter of indicator 128, the one or more perimeter edges of cover 122 and base 132 may be adhered or otherwise fastened to intermediate layer 130 to substantially encapsulate indicator 128. In some examples, intermediate layer 130 may include any one or more of the materials described above in reference to cover 122. In some examples, intermediate layer 130 may include a sterilant impermeable layer, a microorganism barrier layer, and/or a color-enhancing layer. The color-enhancing layer may include any suitable material configured to improve visualization of a color change of at least a portion of indicator 128 in response to exposure to a sterilant during sterilization. In some examples, a color enhancing layer may be adjacent one or more of cover 122 and/or base 132.

In some examples, intermediate layer 130 may define an adhesive configured to adhere cover 122 to base 132. The adhesive may include, for example, a pressure sensitive adhesive, a hot-melt adhesive, a structural adhesive, a thermoplastic, a thermoset polymer, an epoxy, or an adhesive suitable for use in steam, ethylene oxide, dry heat, or vaporized hydrogen peroxide sterilization procedures. In some examples, at least one of cover 122 and/or base 132 may be fastened to at least a portion of intermediate layer 130 using other fastening methods, such as, for example, thermal welding, sonic welding, heat-sealing, mechanical fasteners, or other suitable fastening techniques. In some examples, substantially encapsulating indicator 128 may prevent a sterilant in sterilization chamber 118 from contacting indicator 128 without the sterilant first entering internal cavity 110 of enclosure 104.

Indicator 128 may include at least one of a chemical indicator, a biological indicator, or an indicator configured to provide an indication of an exposure to a sterilant. In some examples, indicator 128 may include an Attest VH202 Tri-Metric Indicator available from 3M, St. Paul, Minnesota or a 3M Comply SteriGage steam chemical integrator available from 3M, St. Paul, Minnesota Although described herein as a visual indication, in some examples, the indication may include, for example, a change in an electrical signal, a change in an optical signal, or a change in physical phenomena.

Indicator 128, e.g., cavity 138, is fluidly coupled to internal cavity 110 of enclosure 104. For example, base 132 may define one or more apertures 140 fluidly coupling cavity 138 with internal cavity 110 of enclosure 104 of sterilization package 100. In examples in which enclosure 104 includes a soft pack, apertures 140 may allow sterilant to pass from internal cavity 110 into cavity 138 during sterilization. In examples in which enclosure 104 includes a rigid container, apertures 140 may allow sterilant to pass from internal cavity 110, through at least a portion of filter 116 and one or more apertures of apertures 114, into cavity 138 during sterilization.

In some examples, indicator 128 may be fluidly coupled to internal cavity 110 via a sample port 144. For example, sample port 144 may define lumen 146 fluidly coupling internal cavity 110 to cavity 138. Sample port 144 may be coupled to or extending through aperture 140. For example, sample port 144 may extend from a proximal end coupled to aperture 140 of base 132 to a distal end configured to extend into internal cavity 110 of enclosure 104 of sterilization package 100. In some examples, sample port 144 may include a proximal end defining a disc from which lumen

146 extends to a distal end extending into internal cavity 110. The disc may have a diameter larger than a diameter of aperture 140. At least a portion of base 132 adjacent to the disc may be configured to engage the disc.

In some examples, an external surface of at least a portion of sample port 144 may define a neck. The neck of sample port 144 may be configured to engage a locking mechanism. The locking mechanism may be configured to secure sample port 144 to enclosure 104 in a tamper-resistant manner. For example, in examples in which enclosure 104 includes a rigid container having a removable lid, sample port 144 may be positioned to extend through aperture 140. The locking mechanism may be engaged with sample port 144 to secure sample port 144 to the lid. Once the lid is closed on the rigid container, the locking mechanism is disposed within internal cavity 110. Hence, sample port 144 may not be disengaged without opening the rigid container. As discussed above, sterilization indicator 102 may be adhered to or otherwise fastened to sample port 144. In this way, sample port 144 may be used to secure sterilization indicator 102 to exterior surface 106 of enclosure 104 of sterilization package 100.

In some examples, sample port 144 may include a sterilant-permeable microorganism barrier disposed within lumen 146. The sterilant-permeable microorganism barrier may be configured to allow sterilant to pass from internal cavity 110 to cavity 138 and prevent microorganisms from passing from cavity 138 into internal cavity 110. The sterilant-permeable microorganism barrier may include, for example, one or more of the flexible materials describe above in reference to the soft pack enclosure 104. In this way, the sterilant-permeable microorganism barrier may reduce potential contamination of internal cavity 110 from sterilization indicator 102.

In some examples, the distal end of sample port 144 may define an incisive tip configured to puncture enclosure 104. For example, the incisive distal end of sample port 144 may be configured to puncture exterior surface 106 of a soft pack enclosure 104. Forming sample port 144 to define an incisive tip may enable, after wrapping articles in a soft pack enclosure 104, sterilization indicator 102 to be affixed to enclosure 104 by puncturing enclosure 104 with sample port 144 and adhering base 132 to exterior surface 106 of enclosure 104.

In some examples, sterilization indicator 102 may include a seal 142 configured to form a sterilant barrier and/or microorganism barrier between an exterior of sterilization indicator 102 and cavity 110 of sterilization package 100 and/or cavity 138 of sterilization indicator 102. The exterior of sterilization indicator 102 may include, for example, any one or more of surface 124 of cover 122, surface 134 of base 132, or another surface of cover 122, intermediate layer 130, and/or base 132 exterior to cavity 138. In some examples, seal 142 may be disposed on a surface of cover 122 or base 132. Seal 142 may extend at least around a perimeter of aperture 140, such as a perimeter of cover 122 and/or base 132. In examples in which cover 122 is integrally formed with intermediate layer 130, seal 142 may be disposed on a lower surface (e.g., surface 126) of cover 122 such that at least a portion of the edges of cover 122 are configured to couple with exterior surface 106 of enclosure 104 of sterilization package 100. In examples in which the proximal end of sample port 144 defines a disc, seal 142 may be disposed on the disc, e.g., between the disc and exterior surface 106 of enclosure 104.

Seal 142 may include any suitable material configured to form a sterilant barrier and/or microorganism barrier between an exterior of sterilization indicator 102 and cavity 110 of sterilization package 100 and/or cavity 138 of sterilization indicator 102. For example, seal 142 may include a pressure sensitive adhesive, an elastomeric material, silicone, polytetrafluoroethylene, nitrile, neoprene, ethylene propylene diene monomer rubber, fluorocarbon, or combinations thereof.

In some examples, sterilization indicator 102 may include a process challenge or be part of a process challenge device. The process may be configured to resist passage of a sterilant from internal cavity 110 to cavity 138 during sterilization. The process challenge may include, for example, a channel fluidly coupling internal cavity 110 to cavity 138. The channel may define a tortuous path that, relative to a substantially straight lumen or a non-tortuous lumen, may slow movement of the sterilant, thereby limiting exposure of indicator 128 to the sterilant. In some examples, the process challenge may be configured to represent a path of travel of sterilant through one or more lumens of a medical device. In some examples, lumen 146 of sample port 144 may define the process challenge.

Figure 2A:
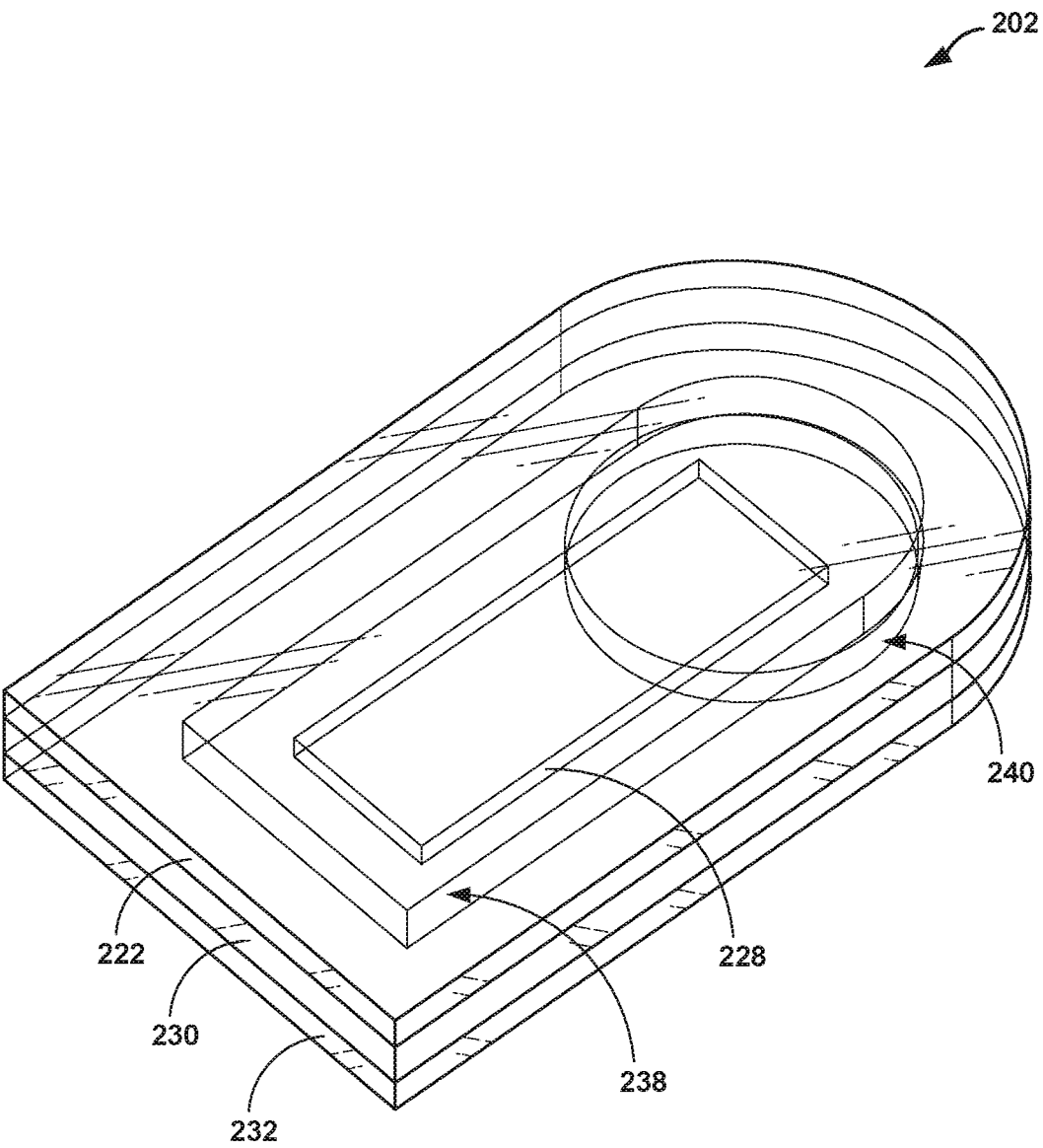
FIGS. 2A-2C are conceptual diagrams illustrating several views of an example sterilization indicator.
Figure 2B:
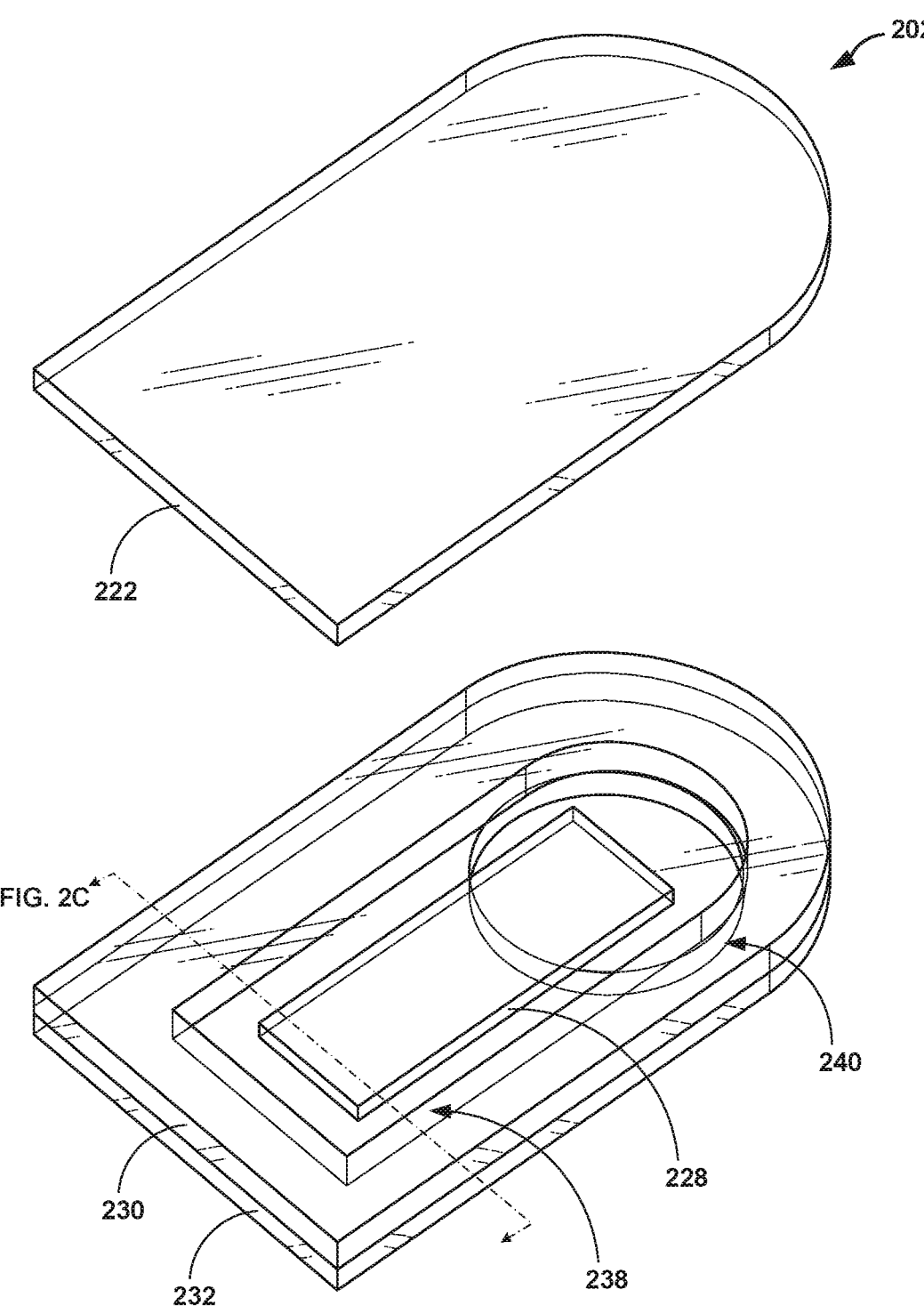
Figure 2C:
Figure 2C:
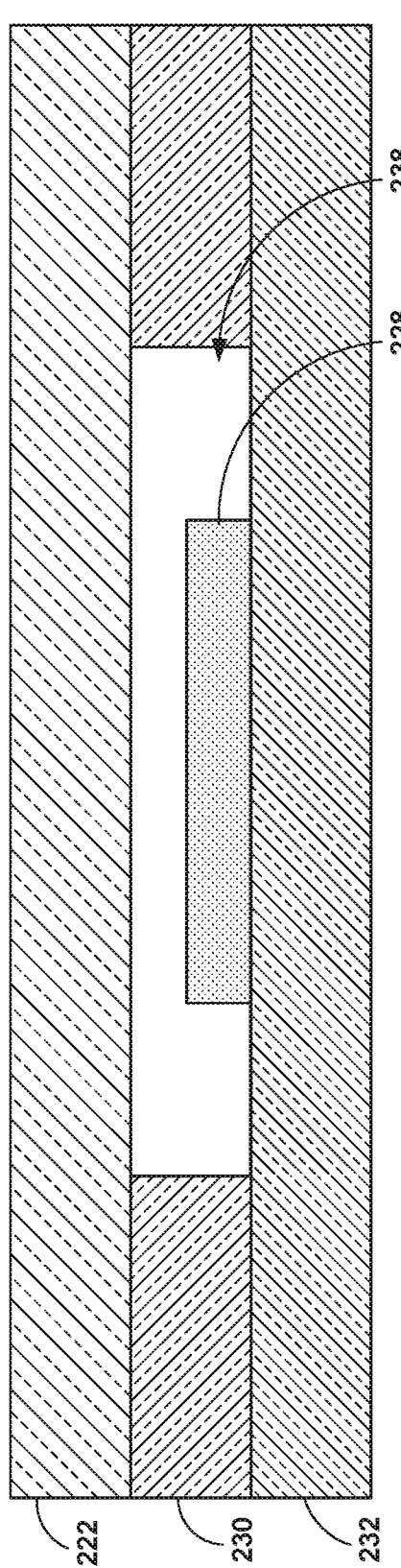

FIGS. 2A-2C are conceptual diagrams illustrating several views of an example sterilization indicator 202. Sterilization indicator 202 may be the same as or substantially similar to sterilization indicator 102 described above in reference to FIG. 1, except for the differences described herein.

Sterilization indicator 202 includes a cover 222, an indicator 228, an intermediate layer 230, and a base 232. As discussed above in reference to FIG. 1, cover 222 and base 232 extend in substantially parallel planes. At least one of cover 222 or base 232 may be integrally formed with, adhered to, or otherwise fastened to at least a portion of intermediate layer 230 to define a cavity 238 that is configured to receive indicator 228.

In some examples, indicator 228 may be adhered to or otherwise fastened to a surface of cover 222 or a surface of base 232 (FIG. 2C). In some examples, indicator 228 may include a coating applied to a surface of cover 222 or a surface of base 232. In some examples, indicator 228 may be removable or replaceable. For example, as illustrated in FIG. 2B, cover 222 may be removable. After removing cover 222, indicator 228, which may include a spent indicator having been exposed to a sterilant, may be replaced with a fresh indicator that has not been exposed to a sterilant. In this way, sterilization indicator 202 may define a housing and a replaceable indicator. By enabling replacement of indicator 228, indicator 202 may reduce operating costs for a Sterile Processing Department compared to using sterilization indicators without replaceable indicators.

Although not illustrated in FIGS. 2A-2C, in examples in which cover 222 is removable, cover 222 may be fixable to base 232 and/or intermediate layer 230 by one or more hinges, clips, or other mechanical fasteners. Additionally, or alternatively, sterilization indicator 202 may include one or more seals between cover 222 and base 232 and/or intermediate layer 230. The one or more seals may be substantially the same as or similar to seal 142 described above in reference to FIG. 1.

In some examples, base 232 may include an adhesive bottom layer (e.g., opposing the surface of base 232 that is adjacent to intermediate layer 230 and indicator 228). The adhesive layer of base 232 may be configured to adhere to a sterilization package (e.g., exterior surface 106 of enclosure 104). For example, the adhesive layer may include a pressure sensitive adhesive, a hot-melt adhesive, a structural adhesive, a thermoplastic, a thermoset polymer, an epoxy, or an adhesive suitable for use in steam, ethylene oxide, dry heat, or vaporized hydrogen peroxide sterilization procedures and selected to adhere to an external surface of a sterilization package.

In examples in which the sterilization package includes a soft pack, the adhesive may be selected to migrate into the flexible material of the soft pack during the sterilization process. Migrating may include a first portion of the adhesive remaining adhered to base 232 and an exterior surface of the soft pack and a second portion of the adhesive moving through the flexible material (e.g., between fibers of the flexible material) toward an interior surface of the soft pack. In this way, the adhesive may form a more sterilant-impermeable barrier and a more microorganism-impermeable barrier (e.g., between an exterior of the soft pack and an interior of the soft pack) compared to sterilization indicator 202 including an adhesive that does not migrate into the flexible material of the soft pack during the sterilization process. Additionally, or alternatively, the adhesive may prevent, or at least reduce an amount of, sterilant from traversing only the flexible material of the soft pack to enter cavity 238. That is, the adhesive may force sterilant entry into cavity 238 via aperture 240 of base 232 from an interior cavity of the soft pack.

Figure 3A:
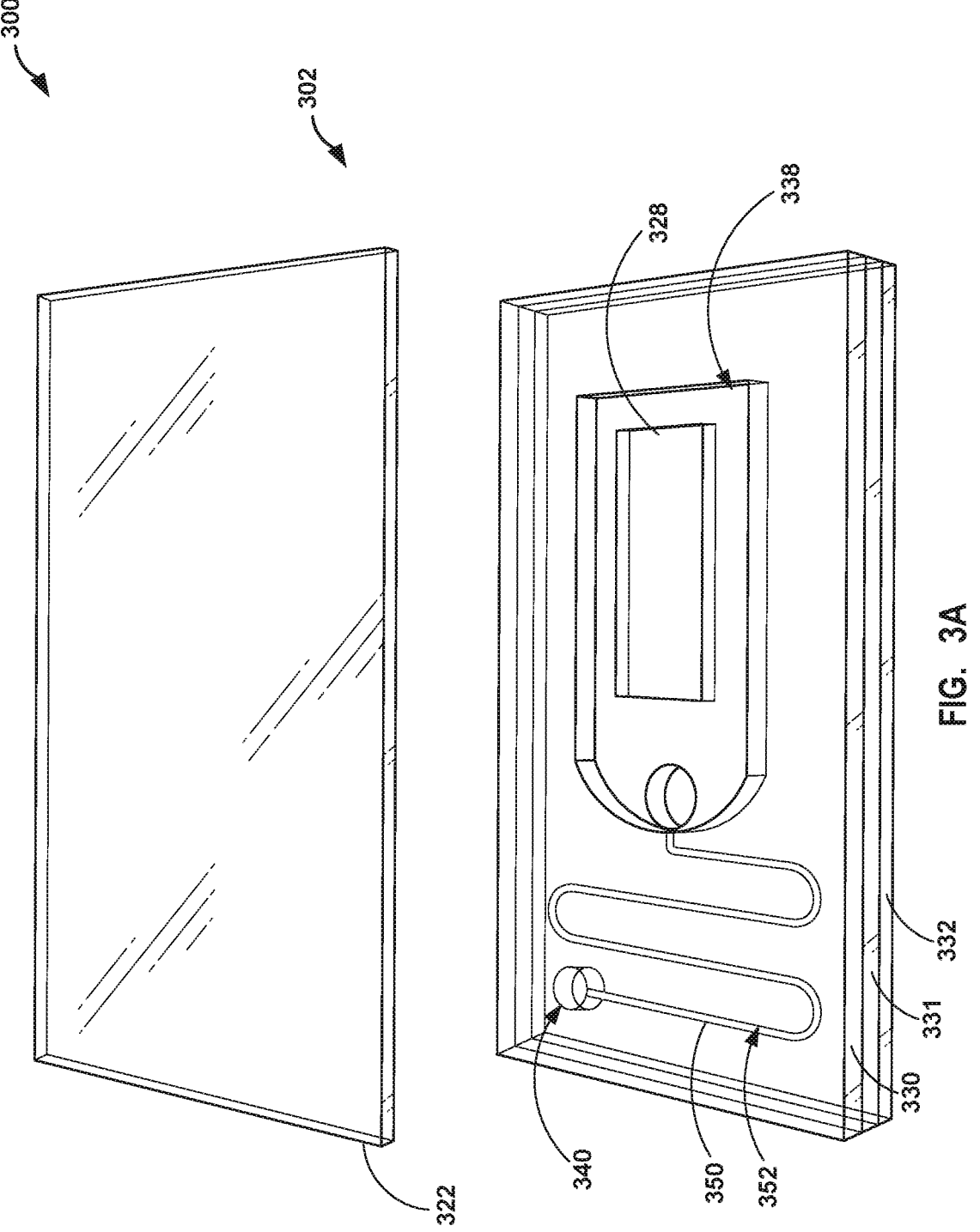
FIGS. 3A and 3B are conceptual diagrams illustrating perspective views of an example sterilization indicator including a process challenge device.
Figure 3B:
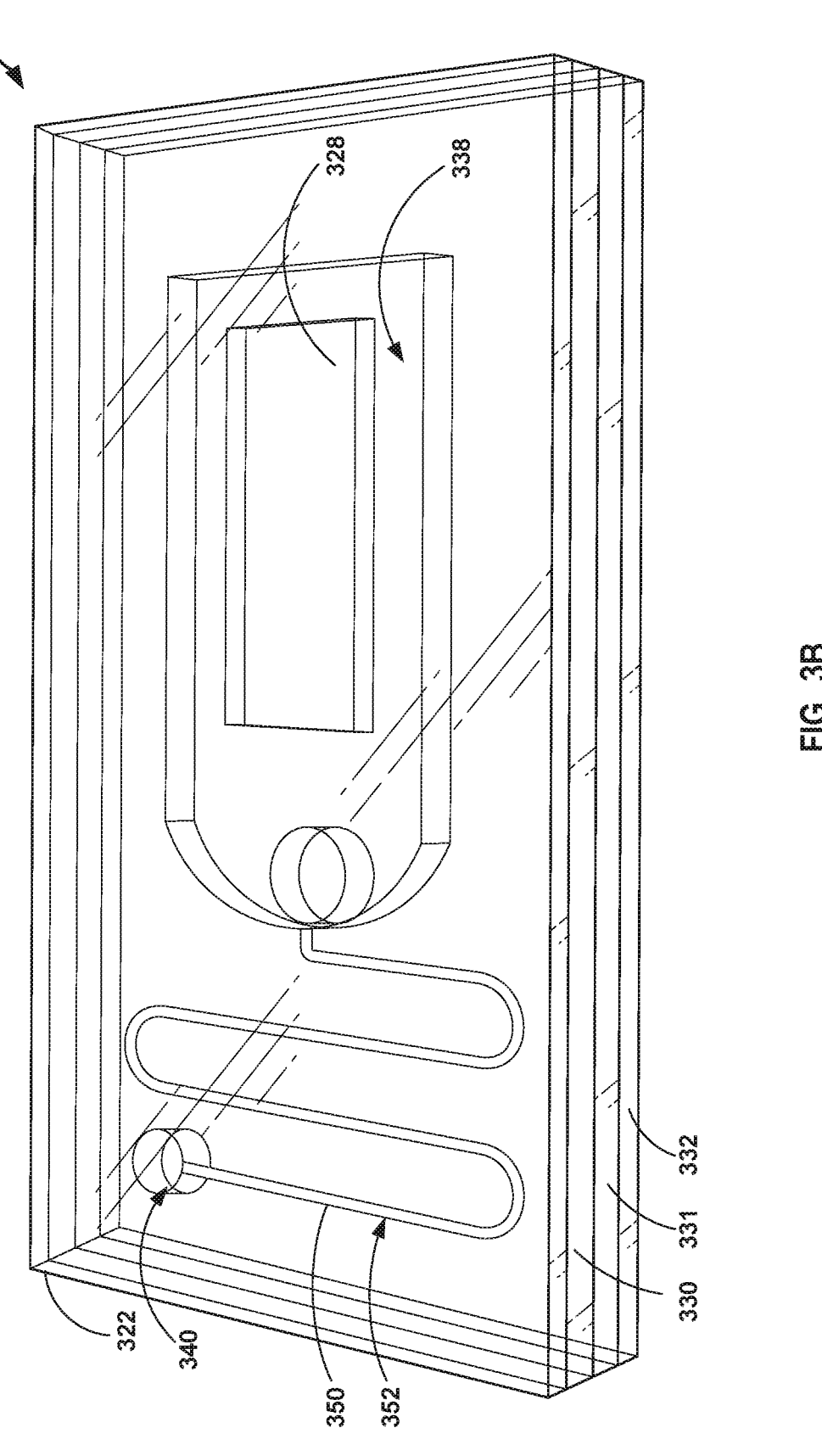

FIGS. 3A and 3B are conceptual diagrams illustrating perspective views of an example process challenge device 300 containing a sterilization indicator 302 including a process challenge 350. Sterilization indicator 302 may be the same as or substantially similar to sterilization indicator 102 and/or 202 described above in reference to FIGS. 1-2C, respectively, except for the differences described herein. Process challenge 350 is configured to restrict the flow of a sterilant to indicator 328 using a tortuous path from aperture 340 of base 332 to cavity 338. The tortuous path may be configured to represent a path of sterilant through one or more lumens of a medical device. For example, endoscopes often include a long, narrow channel through which the sterilant must pass in order to expose all surfaces to the sterilant for a time sufficient to cause sterilization. The tortuous path of process challenge 350 may be configured to represent a path of sterilant through the long, narrow channel of the endoscope.

In some examples, process challenge 350 may be integrally formed with one or more components of process challenge device 300, such as sterilization indicator 302. For example, process challenge device sterilization indicator 302 includes a cover 322, a first intermediate layer 330 adjacent cover 322, a second intermediate layer 331, and a base 332 adjacent second intermediate layer 331. At least one of cover 322, first intermediate layer 330, a second intermediate layer 331, or a base 332 may define a cavity 352 that includes a tortuous path from aperture 340 of base 332 to cavity 338. In some examples, cavity 352 may be formed in at least one of cover 322, first intermediate layer 330, a second intermediate layer 331, or a base 332 by milling, laser etching, lithography, or subtractive manufacturing techniques suitable for use with the materials of process challenge device 300 and resolution required for cavity 352. In other examples, process challenge 350 may be separately formed from, and attachable to, process challenge device 300. For example, process challenge 350 may be adhered to or otherwise mechanically coupled to sterilization indicator 302 to fluidly coupled aperture 340 to an internal cavity of an enclosure.

As illustrated in FIGS. 3A and 3B, second intermediate layer 331 may define cavity 352, whereas first intermediate layer 330, together with cover 322 and second intermediate layer 331, may define cavity 338. The tortuous path of cavity 352 may include any suitable shape. For example, a shape of the tortuous path may include a serpentine shape, one or more necks or narrowed portions, or zigzags. Cavity 352 may extend entirely within a plane defined by cover 322, first intermediate layer 330, a second intermediate layer 331, or a base 332, or may extend between two or more of cover 322, first intermediate layer 330, a second intermediate layer 331, or a base 332.

In some examples, the process challenge 350 may include a heat-transfer modulating body adjacent indicator 328. The heat-transfer modulating body may be configured to slow a rate at which indicator 328 comes to the temperature of a given sterilization process. The heat-transfer modulating body may be integrally formed with at least a portion of process challenge device 300, e.g., base 332, or a separate component that can be included with process challenge device 300 or added or removed from process challenge device 300. In some examples, at least a portion of the heat-transfer modulating body may surround at least a portion of indicator 328. In some examples, the heat-transfer modulating body may increase the time required for the sterilant to contact the indicator sufficiently to bring about an indication that sterilization conditions have been achieved, at least with respect to a temperature of the sterilization conditions.

In some examples, process challenge 350 and/or cavity 338 may include a selected volume of gas, for example, air, nitrogen, carbon dioxide, or another inert gas. The volume of gas contained within process challenge 350 and/or cavity 338 may provide a resistance to the sterilant to contribute, at least in part, to an operation of process challenge 350. The resistance may correlate with sterilization of a variety of products and articles and quantities thereof. In some examples, displacement of the gas may enable the sterilant to fill cavity 338 and contact indicator 328.

In some examples, process challenge device 300 may include a port in fluid communication with the internal cavity of the enclosure, such that condensate can exit out of cavity 338 through the port. Additionally, or alternatively, process challenge device 300 may include an absorbent material within cavity 338, e.g., adjacent indicator 328. The absorbent material may be configured to absorb condensate. Reducing the amount of condensate, when present, that may contact indicator 328 may increase the reproducibility of an indication by indicator 328 that sterilizing conditions have or have not been achieved.

Figure 4:
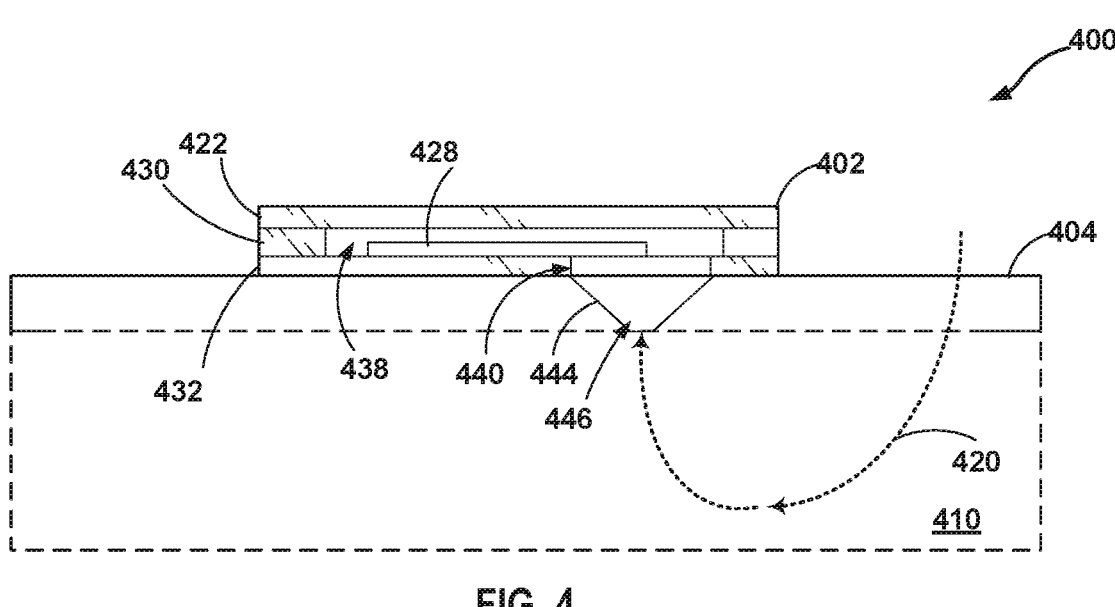
FIG. 4 is a conceptual diagram illustrating an example sterilization package that includes a sterilization indicator positioned on an exterior surface of an enclosure.

FIG. 4 is a conceptual diagram illustrating an example sterilization package 400 that includes a sterilization indicator 402 positioned on an exterior surface of an enclosure 104. Sterilization indicator 402 may be the same as or substantially similar to sterilization indicators 102, 202, 302, and/or process challenge device 300 described above in reference to FIGS. 1-3B, respectively, except for the differences described herein.

Enclosure 404 defines an internal cavity 410. Sterilization indicator 402 includes cover 422 and base 432 adjacent to indicator 428, and intermediate layer 430 extending between cover 422 and base 432. Intermediate layer 430 may define a cavity 438 configured to receive at least a portion of indicator 428. Indicator 428, e.g., cavity 438, may be fluidly coupled to internal cavity 410 via lumen 446 defined by sample port 444 and aperture 440 defined by base 432. Sample port 444 may be tapered. During sterilization, sterilant may move from the sterilization chamber into internal cavity 410 as illustrated by dashed arrow 420. From internal cavity 410, the sterilant may move into sterilization indicator 402.

Figure 5:
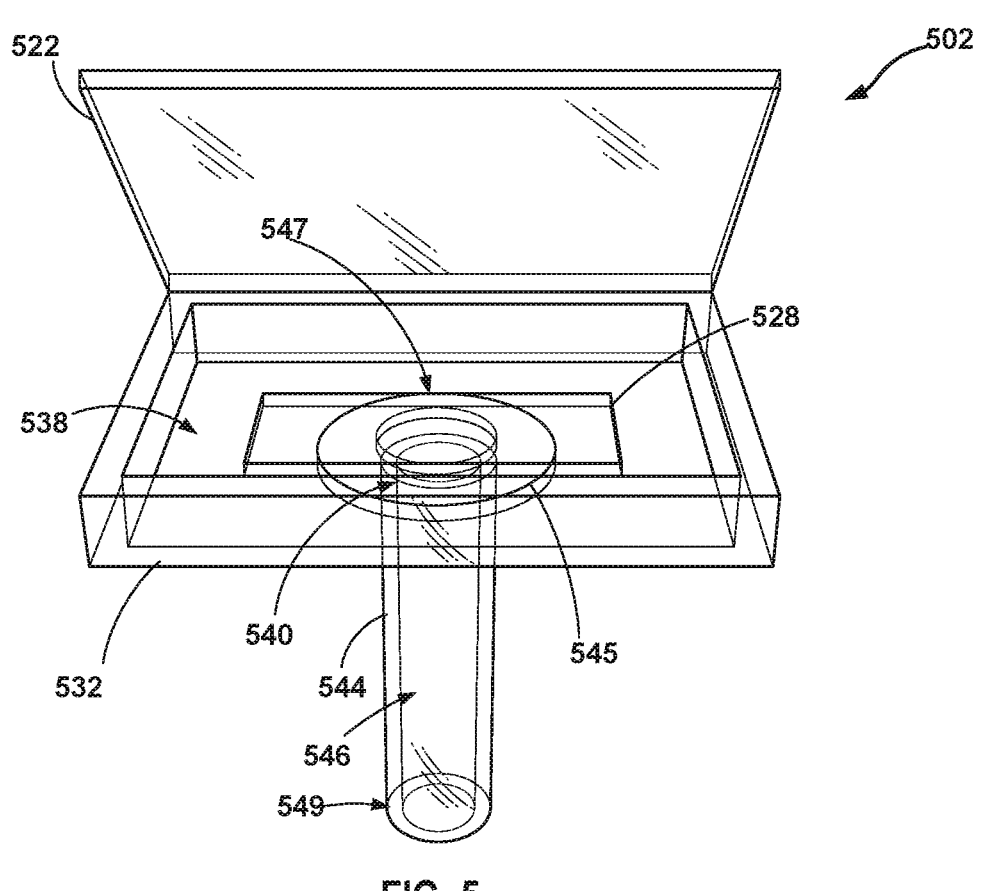
FIG. 5 is a conceptual diagram illustrating a perspective view of an example sterilant indicator.

FIG. 5 is a conceptual diagram illustrating a perspective view of an example sterilization indicator 502. Sterilization indicator 502 may be the same as or substantially similar to sterilization indicators 102, 202, 302, 402, and/or process challenge device 300, described above in reference to FIGS. 1-4, respectively, except for the differences described herein.

Sterilization indicator 502 includes a cover 522, an indicator 528, and a base 532. In some examples, sterilization indicator 502 may include an intermediate layer, as discussed above. At least one of cover 522 or base 532 may define a cavity 538 that is configured to receive indicator 528. Cover 522 may be movable between a closed position and, as illustrated in FIG. 5, an opened position that allows removal of indicator 528. For example, after opening cover 522, indicator 528, which may include a spent indicator having been exposed to a sterilant, may be replaced with a fresh indicator that has not been exposed to a sterilant. By enabling replacement of indicator 528, sterilization indicator 502 may be fixed to a sterilization package.

In some examples, sample port 544 may include a proximal end 547 defining a disc 545 from which lumen 546 extends to a distal end 549 extending into internal cavity 110. The disc may have a diameter larger than a diameter of aperture 540. At least a portion of base 532 adjacent to the disc may be configured to engage disc 545.

Figure 6A:
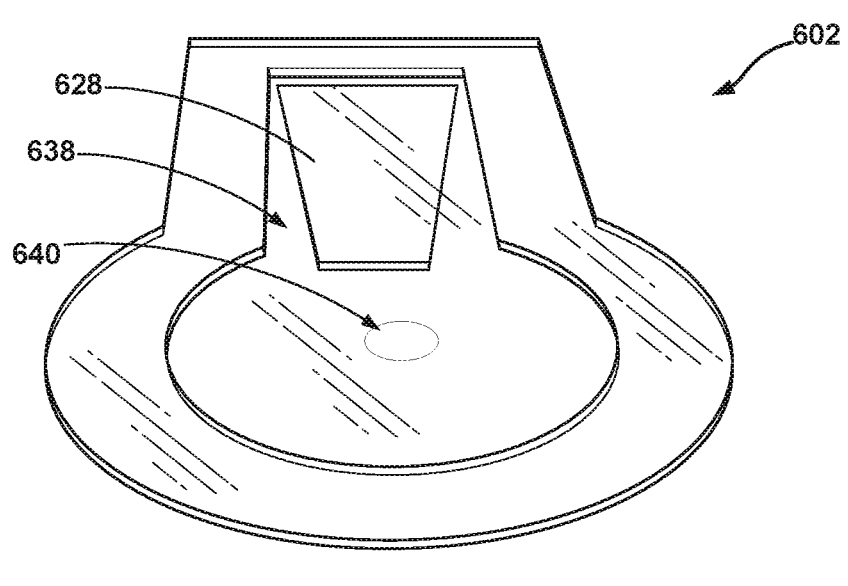
FIGS. 6A and 6B are conceptual diagrams illustrating perspective views of an example sterilization indicator.
Figure 6B:
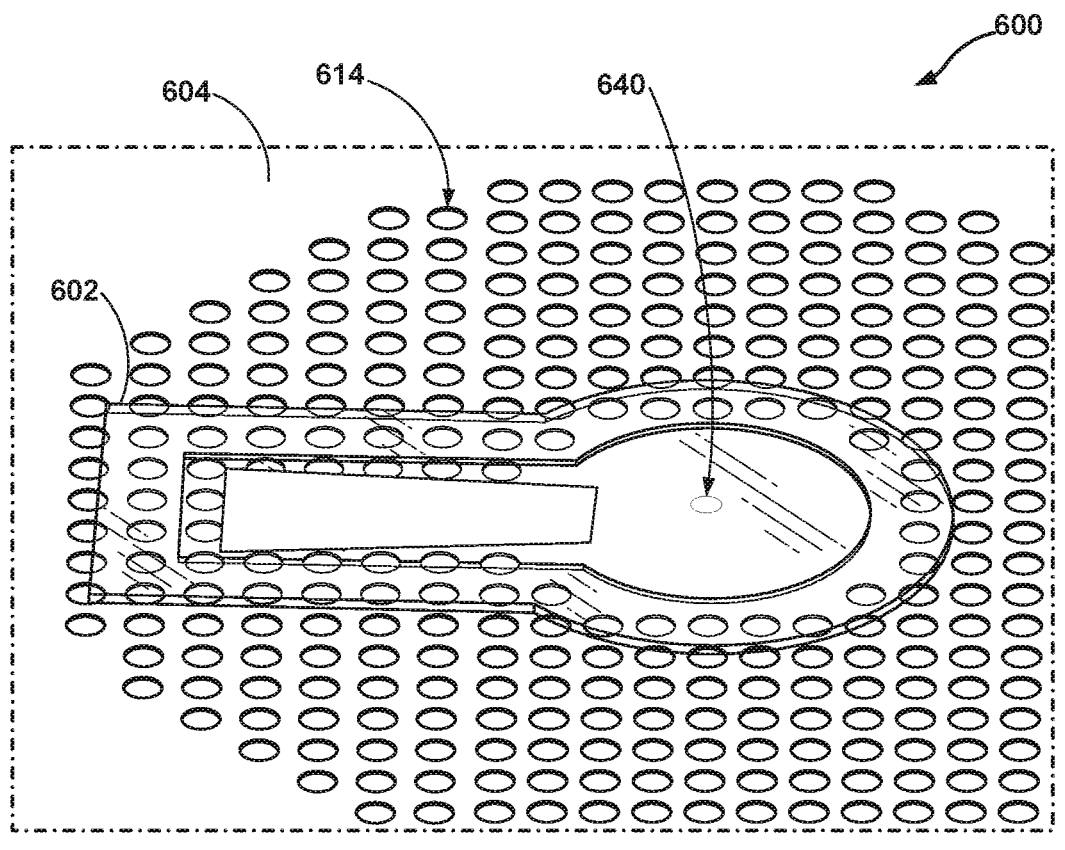

FIGS. 6A and 6B are conceptual diagrams illustrating perspective views of an example sterilization indicator 602. Sterilization indicator 602 may be the same as or substantially similar to sterilization indicators 102, 202, 302, 402, 502, and/or process challenge device 300, described above in reference to FIGS. 1-5, respectively, except for the differences described herein.

Sterilization indicator 602 defines aperture 640 and cavity 638. As illustrated in FIG. 6B, aperture 640 is configured to fluidly couple cavity 638 to an internal cavity of enclosure 604 of sterilization package 600. For example, a shape and size of aperture 640 may be selected to be the same as or substantially similar to a shape and size of a lumen of a sample port and/or positionable over one or more of apertures 614 defined by enclosure 604. Cavity 638 is configured to receive indicator 628. As discussed above, sterilization indicator 602 may include a multi-layer laminate structure including a plurality of polymeric films housing indicator 628 in cavity 638 into which sterilant can be passed only through a sample port via aperture 640.

Figure 7:
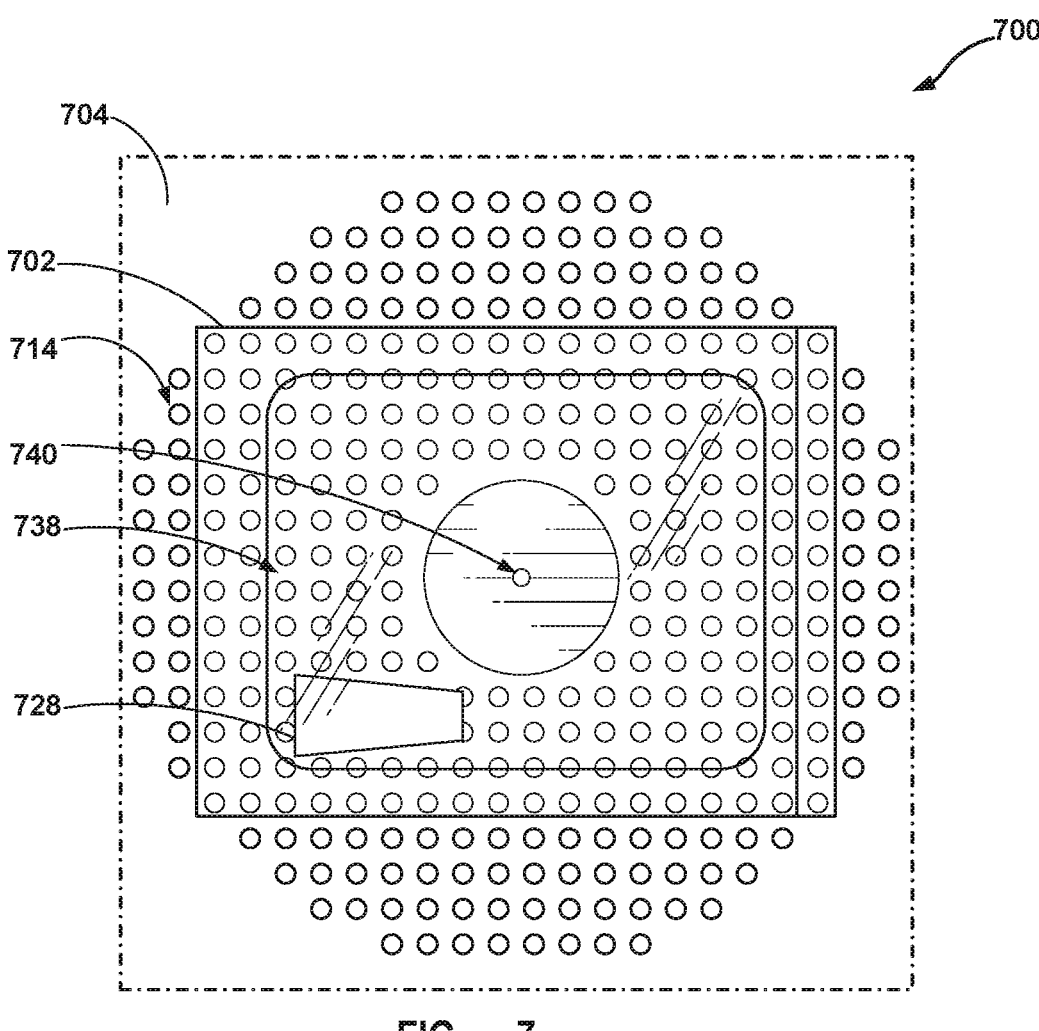
FIG. 7 is a conceptual diagram illustrating a plan view of a portion of an example sterilization package including a clamshell sterilization indicator.

FIG. 7 is a conceptual diagram illustrating a plan view of a portion of an example sterilization package 700 including a sterilization indicator 702. Sterilization indicator 702 may be the same as or substantially similar to sterilization indicators 102, 202, 302, 402, 502, 602, and/or process challenge device 300, described above in reference to FIGS. 1-6B, respectively, except for the differences described herein.

For example, sterilization package 700 includes an enclosure 704 defining a plurality of apertures 714. Sterilization indicator 702 is positioned on enclosure 704. Sterilization indicator 702 includes two layers of flexible polymeric film. Perimeter edges of the two layers of the flexible polymeric film may be sealed together, e.g., as discussed above, to form a clamshell construction. The clamshell construction may define cavity 738, which is configured to receive indicator 728. Aperture 740 is configured to fluidly couple cavity 738 to an internal cavity of enclosure 704. In some examples, the clamshell construction of sterilization indicator 702 may be less expensive and/or less time consuming to manufacture compared to other sterilization indicators, such as a sterilization indicator having a laminate structure.

FIGS. 8A through 8E are conceptual diagrams illustrating example components of a sterilization package 800. Sterilization package 800 may be the same as or substantially similar to sterilization packages 100, 400, 600, and/or 700, except for the differences described herein. For example, sterilization package 800 may include one or more components of sterilization indicators 102, 202, 302, 402, 502, 602, 702, and/or process challenge device 300 sterilization indicators.

Figure 8A:
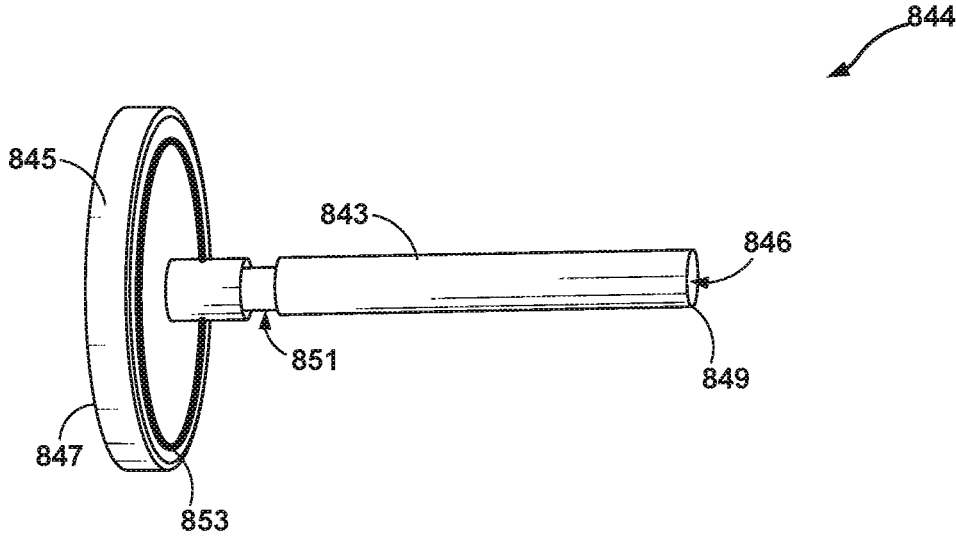
FIGS. 8A through 8E are conceptual diagrams illustrating example components of a sterilization package.

As illustrated in FIG. 8A, sample port 844 includes an elongate tube 843 and a disc 845. Sample port 844 extends from a proximal end 847 to a distal end 849. Proximal end 847 includes disc 845 from which elongate tube 843 extends to distal end 849.

Elongate tube 843 defines lumen 846 and neck 851. Lumen 846 is configured to extend into an internal cavity of enclosure 804 of sterilization package 800. Neck 851 is configured to engage a locking mechanism 860, as illustrated in FIG. 8B.

Figure 8C:
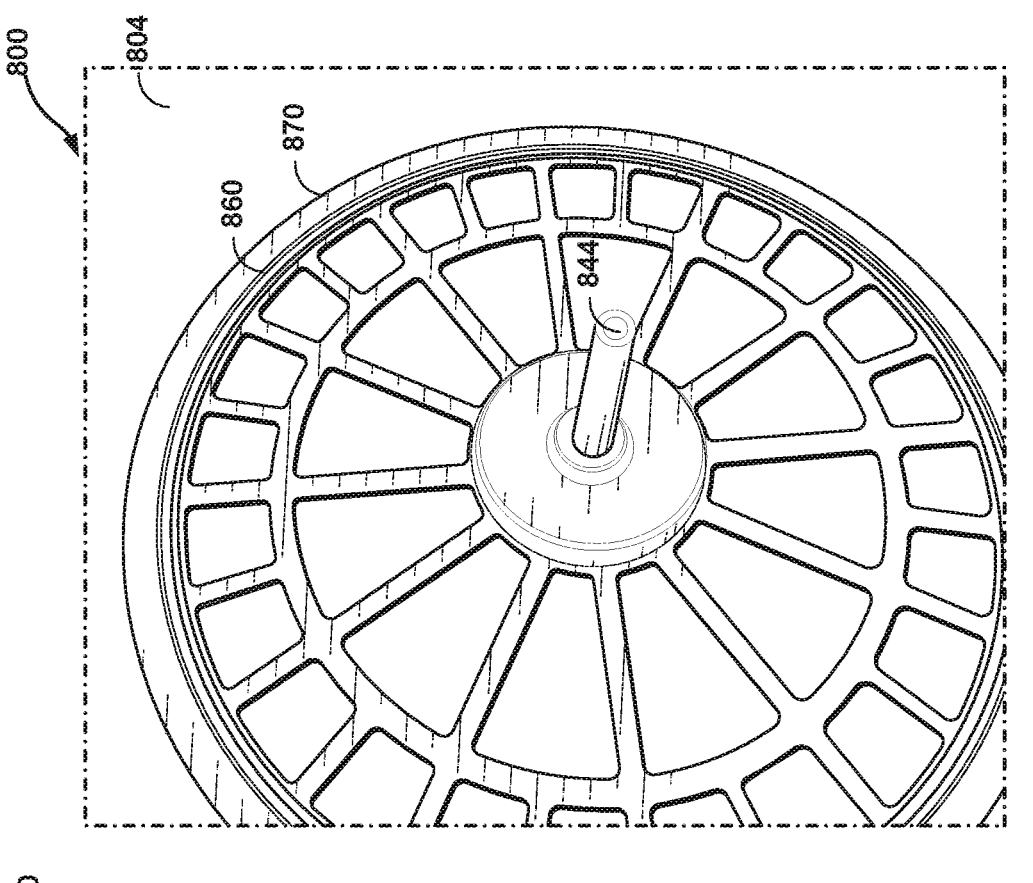

In some examples, locking mechanism 860 may include a frame 862. As illustrated in FIG. 8C, frame 862 may be configured to secure a sterilant-permeable, microorganism barrier 870 (filter 870) to a portion of enclosure 804. For example, frame 862 when engaged with an interior surface of enclosure 804 may secure filter 870 to sterilant-permeable region 812 of enclosure 804 defining apertures 814 (FIG. 8E). In this way, frame 862 may enable enclosure 804 to define one or more sterilant-permeable and microorganism-impermeable pathways from an exterior to an interior of enclosure 804.

Figure 8B:
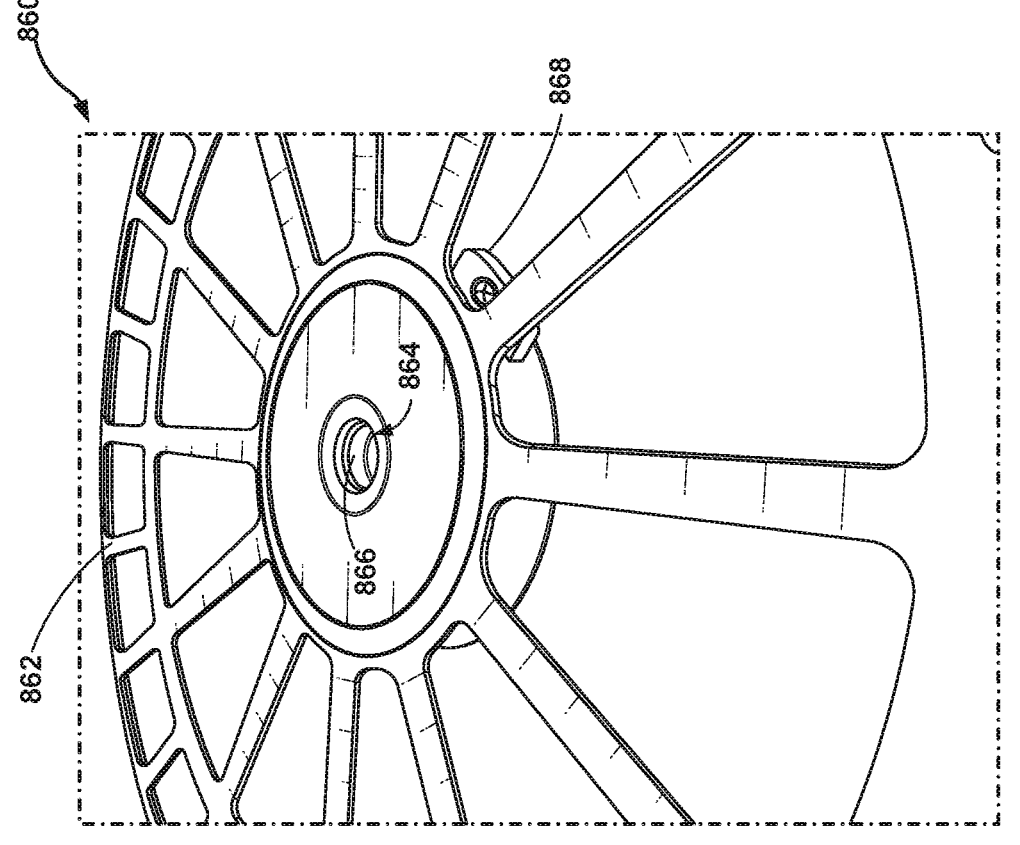
Figure 8D:
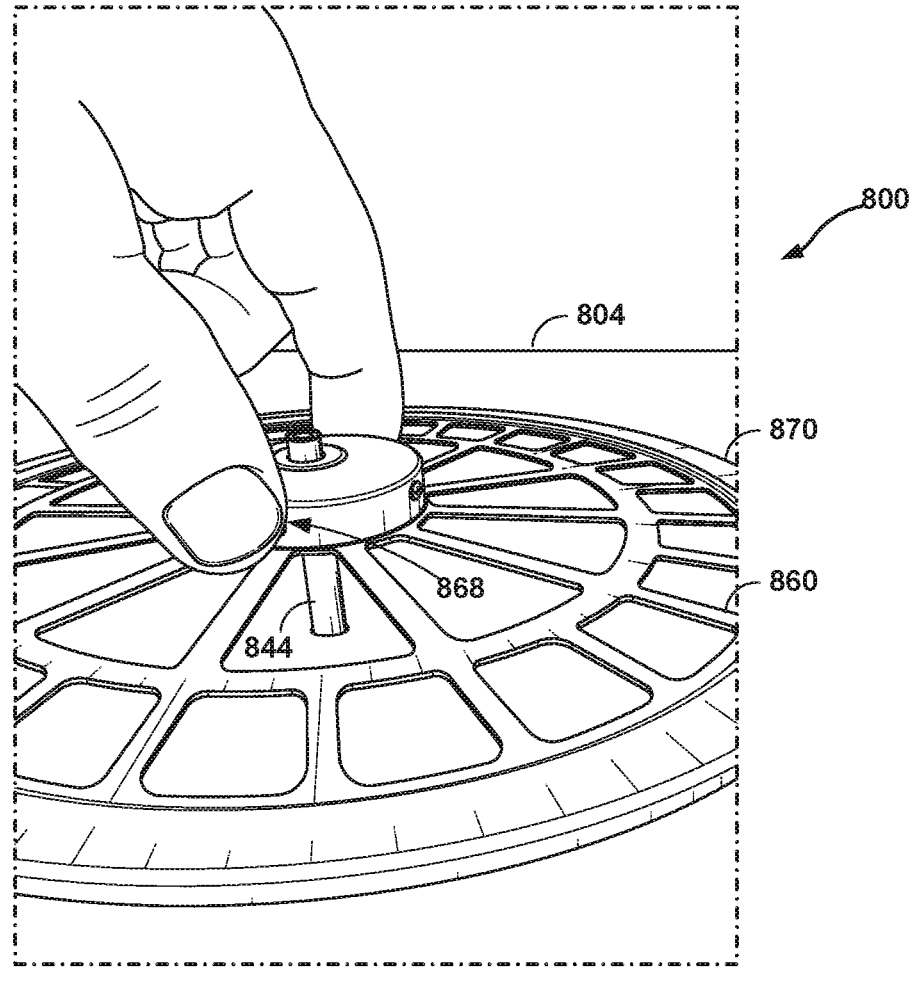
Figure 8E:
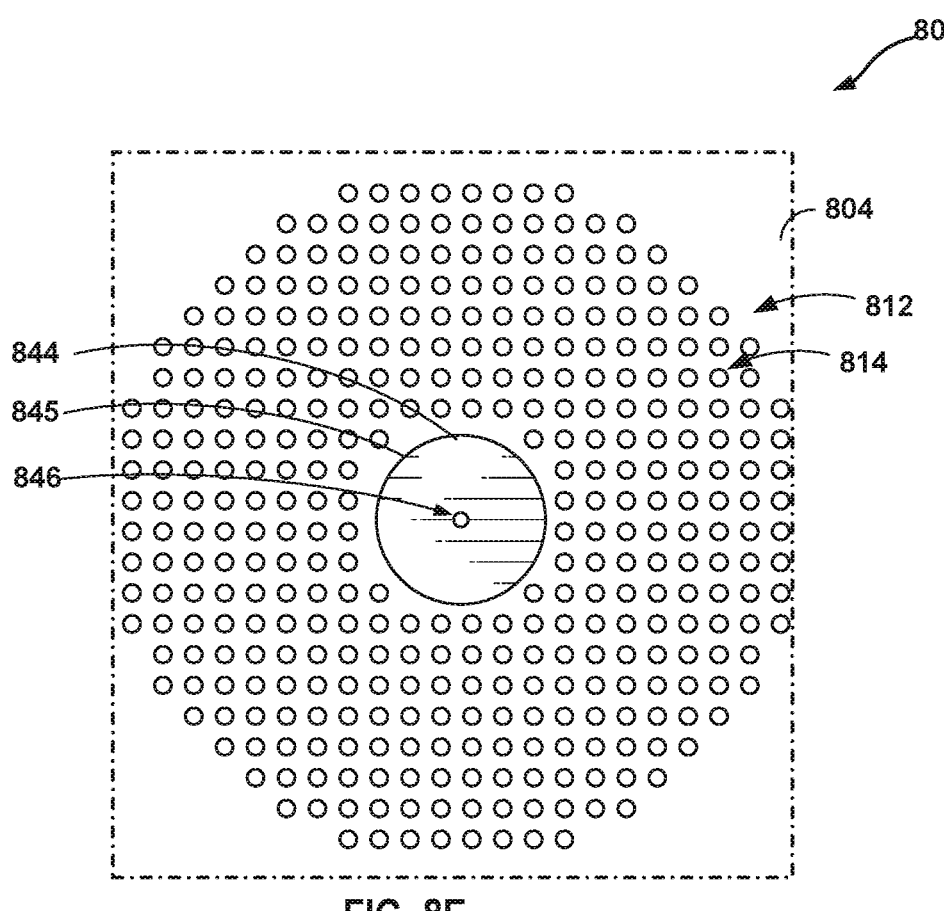

As illustrated in FIG. 8B, locking mechanism 860 may define an aperture 864. Aperture 864 is configured to receive at least a portion of elongate tube 843 of sample port 844 therethrough. For example, elongate tube 843 may be passed through aperture 864 until neck 851 engages locking member 866 of locking mechanism 860. In some examples, locking member 866 may include one or more protrusions shaped to fit within neck 851. Locking mechanism 860 may include one or more springs coupled to locking members 866. The one or more springs may be configured to urge locking members toward a locked configuration. For example, the locked configuration may include a position of locking members 866 that engage neck 851 of sample port 844. In some examples, locking mechanism may include one or more levers 868 mechanically coupled to respective locking members 866. Levers 868 may be configured to move locking members 866 from a locked configuration to an open configuration. The open configuration may include a position of locking members 866 that allow elongate tube 843 to pass through aperture 864. For example, as illustrated in FIG. 8D, levers 868 may be manipulated to allow elongate tube 843 to be inserted into aperture 864 of locking mechanism 860 and/or to disengage locking members 866 from neck 841.

In some examples, disc 845 may define a recess configured to receive a seal, such as o-ring seal 853. Seal 853 may be configured to, when engaged with enclosure 804, such as by a locking mechanism 860, provide a sterilant barrier and/or microorganism barrier between an exterior and an interior of enclosure 804. In some examples, locking mechanism 860 may be configured to engage neck 851 when o-ring seal 853 is compressed a sufficient amount to form the sterilant barrier and/or microorganism barrier.

FIG. 8E is a plan view of sterilant-permeable region 812 of enclosure 804 that defines apertures 814 and disc 845 of sample port 844 engaged, as discussed above, with an exterior surface of enclosure 804. In this way, locking mechanism 860, elongate tube 843, and seal 853 enable a sterilant to travel from an interior of enclosure 804 into a sterilization indicator and reduce or prevent sterilant from traveling into the interior of enclosure 804 from a point external to enclosure 804. Additionally, or alternatively, by positioning locking mechanism 860 within an interior of enclosure 804, sample port 844 and microorganism barrier 870 may be disengaged only once a lid of enclosure 804 is removed, such as, for example, during instrument set-up for a surgical operation.

Figure 9:
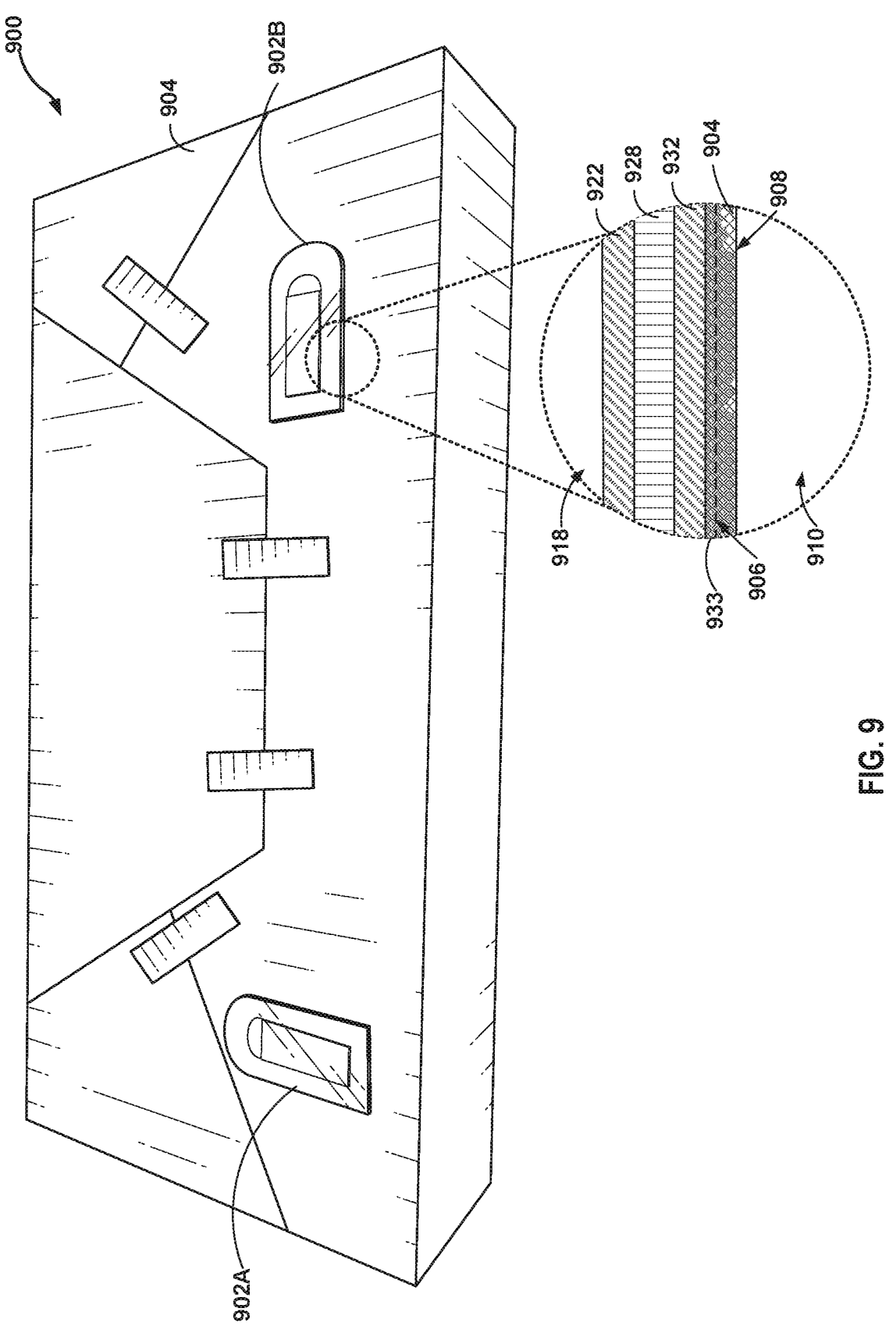
FIG. 9 is a conceptual diagram illustrating a perspective view of a soft pack sterilization package including a plurality of sterilization indicators adhered to the sterilization package.

As discussed above, in some examples, a sterilization indicator may be adhered to a surface of a soft pack sterilization package. FIG. 9 is a conceptual diagram illustrating a perspective view of a soft pack sterilization package 900 including a plurality of sterilization indicators 902A and 902B (collectively, sterilization indicators 902) adhered to enclosure 904 of sterilization package 900. Sterilization package 900 may be the same as or substantially similar to sterilization packages 100, 400, 600, 700, and/or 800, except for the differences described herein. For example, sterilization package 900 may include one or more components of sterilization indicators 102, 202, 302, 402, 502, 602, 702, 802, and/or process challenge device 300.

Enclosure 904 includes folded flexible material taped at seams to define an interior cavity 910. As discussed above, enclosure 904 may define a sterilant-permeable microorganism barrier between interior cavity 910 and sterilization chamber 918 (e.g., external to enclosure 904). Sterilization indicators 902 are configured to adhere to an exterior surface 906 of enclosure 904. For example, as illustrated in the cross-section, sterilization indicators include a cover 922 and base 932 configured to retain indicator 928. Base 932 includes an adhesive layer 933 on a surface of base 932 adjacent to enclosure 904. Adhesive 933 may be configured to migrate at least partially through flexible material of enclosure 904. For example, adhesive layer 933 may be configured to migrate into flexible material of enclosure 904 when exposed to heat, moisture, or pressure. At least a first portion of adhesive layer 933 may remain adhered to base 932 and exterior surface 906 of enclosure 904. At least a second portion of adhesive layer 933 may migrate into the flexible material (e.g., between fibers of the flexible material) toward interior surface 908 of enclosure 904. In this way, adhesive layer 933 may be configured to form a more sterilant-impermeable barrier and a more microorganism-impermeable barrier (e.g., between an exterior 918 of enclosure 904 and interior cavity 910) compared to sterilization indicator 902 including an adhesive that does not migrate into the flexible material of enclosure 904 before or during the sterilization process. Additionally, or alternatively, the adhesive may prevent, or at least reduce an amount of, sterilant from traversing only the flexible material of enclosure 904 to contact indicator 928 without first entering cavity 910.

Figure 10:
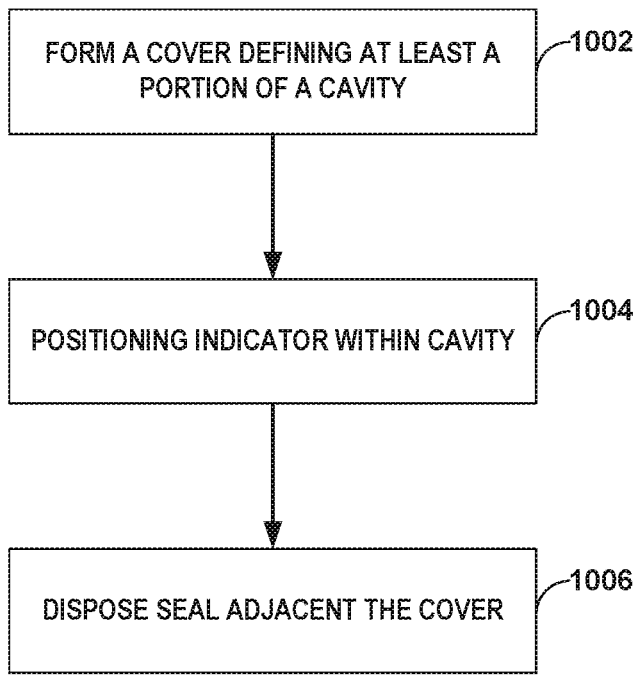
FIG. 10 is a flow diagram illustrating an example technique of forming a sterilization indicator.

FIG. 10 is a flow diagram illustrating an example technique of forming a sterilization indicator. Although the technique illustrated in FIG. 10 will be described in reference to sterilization indicator 102 described in reference to FIG. 1, the technique may be used to form other sterilization indicators, such as any one or more of sterilization indicator 202, 302, 402, 502, 602, 702, 802, 902, and/or process challenge device 300.

The technique illustrated in FIG. 10 includes forming a cover 122 defining at least a portion of a cavity 138 (1002). In some examples, sterilization indicator 102 may include a laminate structure, including, for example, cover 122, intermediate layer 130, and base 132. In examples in which the sterilization indicator includes a laminate structure, forming cover 122 may include laminating base 132 to cover 122, or laminating one or more intermediate layers 130 to cover 122 and laminating base 132 to the one or more intermediate layers 130. As used herein, laminating may include fixing at least a portion of two or more layers by adhering, ultrasonic welding, thermal welding, or other suitable fastening technique.

In some examples, forming cover 122 may include molding cover 122. For example, molding may include injection molding, vacuum forming, or other molding process to produce a selected shape of cover 122. For example, molding cover 122 may include molding cover 122 to define at least a portion of cavity 138. In some examples, forming cover 122 may include molding one or more of intermediate layer 130 and base layer 132.

In some examples, forming cover 122 may include removing material from cover 122. Removing material from cover 122 may include, for example, milling, laser etching, chemical etching, or other substantive manufacturing technique. For example, forming cover 122 may include machining at least a portion of cover 122 to form at least a portion of cavity 138. In some examples, forming cover 122 may include laser etching at least a portion of cover 122, intermediate layer 130, and/or base 132 to form one or more process challenges (e.g., process challenge 350). In some examples, forming cover 122 may include removing material from intermediate layer 130, e.g., to define cavity 138, and/or removing material from base 132, e.g., to define aperture 140.

The technique illustrated in FIG. 10 may include positioning indicator 128 within cavity 138 (1004). Positioning indicator 128 may include positioning indicator 128 into cavity 138, or into a location of cavity 138, before or after forming cover 122 and/or cavity 138. In some examples, positioning indicator 128 within cavity 138 may include placing indicator 128 into cavity 138, or into a location of cavity 138, without adhering or otherwise fixing indicator 128 within cavity 138. In some examples, positioning indicator 128 within cavity 138 may include removing cover 122, positioning indicator 128 within cavity 138, and replacing cover 122. In some examples, positioning indicator 128 within cavity 138 may include adhering indicator 128 to surface 126 of cover 122, surface 134 of base 132, or a surface of intermediate layer 130. In examples in which indicator 128 includes a coating, positioning indicator 128 may include coating surface 126 of cover 122, surface 134 of base 132, or a surface of intermediate layer 130. As used herein, coating to position indicator 128 may include any suitable coating process, such as, for example, spray coating, brush application, ink jet printing, or other additive manufacturing process.

The technique illustrated in FIG. 10 may include disposing seal 142 adjacent the cover (1006). Disposing seal 142 may include disposing an adhesive or an elastomeric material on a surface of one or more of cover 122, intermediate layer 130, or base 132. In some examples, disposing seal 142 may include disposing an adhesive or an elastomeric material on a surface of sample port 144.

In some examples, the technique may include forming sample port 144. Forming sample port 144 may include any suitable additive manufacturing process, e.g., three dimensional printing, and/or subtractive manufacturing process, e.g., milling or machining, to form sample port 144. In some examples, forming sample port 144 may include positioning seal 142 on at least a portion of sample port 144. In some examples, forming sample port 144 may include positioning a sterilant-permeable, microorganism barrier within lumen 146 of sample port 144. In examples in which sample port 144 includes an incisive distal end, forming sample port 144 may include removing material to define the incisive distal end. In examples in which sample port 144 includes a proximal disc (e.g., disc 845) and elongate tube (e.g., elongate tube 843), disc 845 may be integrally formed with elongate tube 843, or separately formed and subsequently fixed, e.g., using an adhesive, welding, or the like. In examples in which sample port 144 includes a neck (e.g., neck 851), forming sample port 144 may include forming neck 841 by, for example, removing material from elongate tube 843.

In some examples, the technique also may include forming enclosure 104 including at least one sterilant-permeable region 112. In some examples, the technique also may include positioning sterilization indicator 102 on at least a portion of the sterilant-permeable region 112. In examples in which enclosure 104 includes a soft pack, positioning sterilization indicator 102 on enclosure 104 may include adhering sterilization indicator 102 to exterior surface 106 of enclosure 104. In examples in which sterilization indicator 102 includes an incisive distal end, positioning sterilization indicator 102 may include piercing, with the incisive distal end, enclosure 104. In examples in which enclosure 104 includes a rigid container, positioning sterilization indicator 102 may include extending at least a portion of sample port 144 through aperture 140 of enclosure and, in some examples, engaging neck 851 with a locking mechanism (e.g., locking mechanism 860) to secure sample port 144 to enclosure 104.

Figure 11:
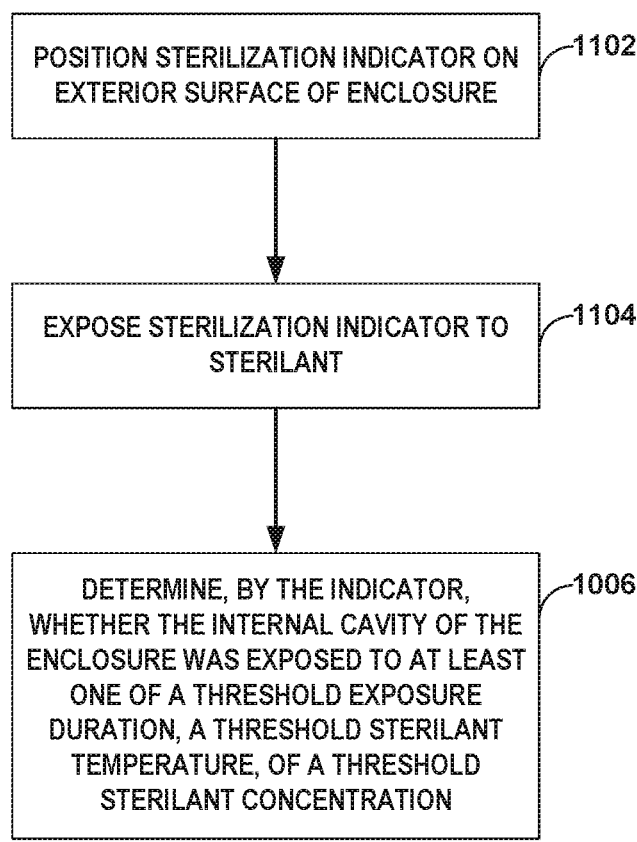
FIG. 11 is a flow diagram illustrating an example technique of using a sterilization indicator.

FIG. 11 is a flow diagram illustrating an example technique of using a sterilization indicator. Although the technique illustrated in FIG. 11 will be described in reference to sterilization package 100 described in reference to FIG. 1, the technique may be used with other sterilization packages and sterilization indicators, such as, any one or more of sterilization indicator 202, 302, 402, 502, 602, 702, 802, 902, and/or process challenge device 300.

The technique illustrated in FIG. 11 includes positioning sterilization indicator 102 on exterior surface 106 of enclosure 104 (1102). At least a portion of exterior surface 106 includes sterilant-permeable region 112. In examples in which enclosure 104 includes a soft pack, positioning sterilization indicator 102 on enclosure 104 may include adhering sterilization indicator 102 to exterior surface 106 of enclosure 104. In examples in which sterilization indicator 102 includes an incisive distal end, positioning sterilization indicator 102 may include piercing, with the incisive distal end, enclosure 104. In examples in which enclosure 104 includes a rigid container, positioning sterilization indicator 102 may include extending at least a portion of sample port 144 through aperture 140 of enclosure and, in some examples, engaging neck 851 with a locking mechanism (e.g., locking mechanism 860) to secure sample port 144 to enclosure 104.

The technique illustrated in FIG. 11 includes exposing sterilization indicator 102 and enclosure 104 to a sterilant at least one of for a selected duration of time, at a selected temperature, or at a selected sterilant concentration (1104). In some examples, exposing sterilization indicator 102 to the sterilant may include using a vacuum to remove air from sterilization chamber 118. Exposing sterilization indicator 102 to the sterilant includes introducing the sterilant into cavity 110, e.g., as illustrated by arrow 120, such that sterilant travels into cavity 138 via lumen 146, e.g., as illustrated by arrow 121. In some examples, at least one of the selected duration of time, the selected temperature, or the selected sterilant concentration may be based, at least in part, on one or more of the type or types of articles to be sterilized, common sterilization practices, the type of enclosure 104 (e.g., rigid container or soft pack), the type of sterilant, or the like.

The technique illustrated in FIG. 11 includes determining, by indicator 128, whether internal cavity 110 of enclosure 104 was exposed to at least one of a threshold exposure duration, a threshold sterilant temperature, or a threshold sterilant concentration (1106). In some examples, determining the exposure of indicator 128 may include comparing a color change of indicator 128 to a legend or a key. For example, a threshold color change of indicator 128 may indicate at least one of the threshold exposure duration, the threshold sterilant temperature, or the threshold sterilant concentration. In some examples, the indication may include, for example, a change in an electrical signal, a change in an optical signal, or a change in physical phenomena. In this way, determining the exposure of indicator 128 may include determining, by processing circuitry coupled to indicator 128, based on a change in an electrical signal or an optical signal, whether internal cavity 110 of enclosure 104 was exposed to at least one of a threshold exposure duration, a threshold sterilant temperature, or a threshold sterilant concentration.

Various embodiments of the invention have been described. These and other embodiments are within the scope of the following claims.

The invention claimed is:

1. A sterilization indicator, comprising:
a cover defining at least a portion of a cavity;
an indicator disposed within the cavity, wherein the indicator is configured to fluidly couple with an internal cavity of a sterilization package and indicate an exposure to a sterilant; and
a seal configured to form a microorganism barrier between an exterior of the cover and the cavity of the sterilization package, wherein the sterilization indicator defines a laminate structure, wherein the cover comprises a cover layer, and wherein the indicator comprises an indicator layer disposed on the cover layer;
a base, wherein the indicator layer is dimensionally smaller than the base, and edges of the base extend beyond the indicator, and wherein at least a portion of the edges of the base are coupled to at least a portion of the edges of the cover, wherein the base defines a second surface opposing the cover, and wherein at least a portion of the second surface of the base is configured to couple with an exterior of the sterilization package; and
a release liner wherein the cover is peripherally bonded to the release liner such that the indicator is disposed between the release liner and the cover.

2. The sterilization indicator of claim 1, wherein the indicator is configured to provide an indication of an effectiveness of a sterilization procedure.

3. The sterilization indicator of claim 1, wherein the seal is disposed on a surface of the cover, and wherein at least a portion of the cover is configured to couple with an exterior of the sterilization package.

4. The sterilization indicator of claim 1, wherein the indicator is dimensionally smaller than the cover, and edges of the cover extend beyond the indicator.

5. The sterilization indicator of claim 4, wherein the sterilization indicator further comprises at least one intermediate layer disposed between the cover and the indicator, and wherein the at least one intermediate layer comprises at least one of a sterilant-impermeable layer, an adhesive layer, or a color-enhancing layer.

6. The sterilization indicator of claim 5, wherein at least a portion of the intermediate layer is configured to couple with an exterior of the sterilization package.

7. The sterilization indicator of claim 1, wherein the base defines an aperture fluidly coupling the indicator with the internal cavity of the sterilization package.

8. The sterilization indicator of claim 7, further comprising a sample port comprising an elongate tube defining a lumen and extending from a proximal end fluidly coupled to the aperture of the base to a distal end configured to extend into the internal cavity of the sterilization package.

9. The sterilization indicator of claim 8, wherein the distal end of the sample port defines an incisive tip configured to puncture an exterior surface of the sterilization package.

10. The sterilization indicator of claim 8, wherein the proximal end of sample port defines a disc configured to couple with the second surface of the base, and wherein the seal is disposed between the disc and the exterior of the sterilization package.

11. The sterilization indicator of claim 8, wherein an external surface of the sample port defines a neck configured to engage a locking mechanism of a sterilization package to secure the sterilization indicator to an exterior surface of the sterilization package.

12. The sterilization indicator of claim 8, wherein the sample port comprises a sterilant-permeable microorganism barrier disposed within the lumen of the sample port.

13. The sterilization indicator of claim 8, further comprising a process challenge device configured to resist passage of the sterilant through the lumen of the sample port.

14. The sterilization indicator of claim 1, wherein the indicator comprises at least one of a chemical indicator or a biological indicator.

15. The sterilization indicator of claim 1, further comprising a process challenge device defining a channel fluidly coupling the indicator to the internal cavity of the sterilization package, wherein the process challenge device is configured to resist passage of the sterilant through the channel.

16. A sterilization package comprising:
an enclosure having an exterior surface and defining an internal cavity, wherein at least a portion of the enclosure comprises a sterilant-permeable region; and
the sterilization indicator of claim 1.

17. The sterilization package of claim 16, wherein the enclosure comprises a flexible, sterilant-permeable microorganism barrier material.

18. The sterilization package of claim 16, wherein the enclosure comprises a rigid container, and wherein at least a portion of the rigid container defines an aperture fluidly coupling the indicator with the internal cavity.

19. A sterilization indicator, comprising:
a cover defining at least a portion of a cavity;
an indicator disposed within the cavity, wherein the indicator is configured to fluidly couple with an internal cavity of a sterilization package and indicate an exposure to a sterilant; and
a seal configured to form a microorganism barrier between an exterior of the cover and the cavity of the sterilization package, wherein the sterilization indicator defines a laminate structure, wherein the cover comprises a cover layer, and wherein the indicator comprises an indicator layer disposed on the cover layer; and a base, wherein the indicator layer is dimensionally smaller than the base, and edges of the base extend beyond the indicator, and wherein at least a portion of the edges of the base are coupled to at least a portion of the edges of the cover, wherein the base defines a second surface opposing the cover, and wherein at least a portion of the second surface of the base is configured to couple with an exterior of the sterilization package;

wherein the base defines an aperture fluidly coupling the indicator with the internal cavity of the sterilization package.

20. A sterilization indicator, comprising:

a cover defining at least a portion of a cavity;

an indicator disposed within the cavity, wherein the indicator is configured to fluidly couple with an internal cavity of a sterilization package and indicate an exposure to a sterilant; and a seal configured to form a microorganism barrier between an exterior of the cover and the cavity of the sterilization package, wherein the sterilization indicator defines a laminate structure, wherein the cover comprises a cover layer, and wherein the indicator comprises an indicator layer disposed on the cover layer;

a base, wherein the indicator layer is dimensionally smaller than the base, and edges of the base extend beyond the indicator, and wherein at least a portion of the edges of the base are coupled to at least a portion of the edges of the cover, wherein the base defines a second surface opposing the cover, and wherein at least a portion of the second surface of the base is configured to couple with an exterior of the sterilization package; and a process challenge device defining a channel fluidly coupling the indicator to the internal cavity of the sterilization package, wherein the process challenge device is configured to resist passage of the sterilant through the channel.

* * * * *